United States Patent [19]

Singer et al.

[11] Patent Number: 5,871,950
[45] Date of Patent: Feb. 16, 1999

[54] METHODS OF TREATING AUTOIMMUNE DISEASES AND TRANSPLANTATION REJECTION

[76] Inventors: Dinah S. Singer, 6404 Ruffin Rd., Chevy Chase, Md. 20815; Leonard Kohn, 9630 Parkwood Dr., Bethesda, Md. 20814; Edna Mozes, 51 Hanachi Harishon, Rehovot, Israel, 76303; Motoyasu Saji, 10228 Rockville Pike, Rockville, Md. 20852; Jocelyn Weissman, 3411 Janet Rd., Silver Spring, Md. 20906; Giorgio Napolitano, 11315 Commonwealth Dr., Rockville, Md. 20852; Fred D. Ledley, 4911 Braesvalley, Houston, Tex. 77096

[21] Appl. No.: 460,886

[22] Filed: Jun. 5, 1995

Related U.S. Application Data

[62] Division of Ser. No. 073,830, Jun. 7, 1993, abandoned.

[51] Int. Cl.⁶ .............................. C12Q 1/02; C12Q 1/00; G01N 33/53; A01N 61/00
[52] U.S. Cl. .............................. 435/29; 435/4; 435/7.1; 435/7.2; 435/7.21; 435/7.24; 435/240.2; 435/240.1; 514/1; 514/885; 514/863; 514/580; 424/184.1; 424/177.1; 424/9.1
[58] Field of Search ............................ 435/29, 4, 1.1, 435/6, 7.24, 240.1, 240.2, 7.1, 7.2, 7.21; 514/1, 885, 863, 580; 424/9.1, 184.1, 177.1

[56] References Cited

U.S. PATENT DOCUMENTS

| | | | |
|---|---|---|---|
| 4,120,649 | 10/1978 | Schechter | 435/1.1 |
| 4,591,604 | 5/1986 | Conrow et al. | 435/1.1 |
| 4,599,203 | 7/1986 | Conrow et al. | 260/506 |
| 4,696,286 | 9/1987 | Cochrum | 435/1.1 |
| 4,727,018 | 2/1988 | Eichner et al. | 435/1.1 |
| 5,010,092 | 4/1991 | Elfarra | 514/359 |
| 5,068,175 | 11/1991 | Prashad | 435/6 |
| 5,087,441 | 2/1992 | Elfarra | 424/10 |
| 5,104,898 | 4/1992 | Hess et al. | 514/557 |
| 5,135,915 | 8/1992 | Czarniecki et al. | 514/21 |
| 5,212,155 | 5/1993 | Calne | 435/1.1 |
| 5,310,742 | 5/1994 | Elias | 514/274 |
| 5,364,762 | 11/1994 | Dornmair et al. | 435/7.24 |

FOREIGN PATENT DOCUMENTS

| | | |
|---|---|---|
| 0487298A2 | 5/1992 | European Pat. Off. |
| 1592453 | 7/1981 | United Kingdom. |
| 92/04033 | 3/1992 | WIPO. |
| 92/08464 | 5/1992 | WIPO. |
| 93/04203 | 3/1993 | WIPO. |

OTHER PUBLICATIONS

Motoyasu Saji et al; J. Clin. Endocrin and Metabolism, V 75, No. 3, pp. 871–878, (1992).

Allen, et al., "The Effect of Methimazole on the Development of Spontaneous Lymphocytic Thyroiditis in the Diabetes–Prone BB/W Rat", *The American Journal of the Medical Sciences*, 1986, vol. 292, No. 5, pp. 267–271, month not available.

Bagnasco, et al., "The Effect of Methimazole on the Immune System is Unlikely to Operate Directly on T Lymphocytes", *J. Endocrinol. Invest.*, 1990, vol. 13, pp. 493–499, month not available.

(List continued on next page.)

*Primary Examiner*—Louise Leary

[57] ABSTRACT

The present invention provides methods for treating autoimmune diseases in mammals and for preventing or treating transplantation rejection in a transplant recipient. The methods of treatment involve the use of drugs capable of suppressing expression of MHC Class I molecules. In particular the use of the drug methimazole to suppress expression of MHC Class I molecules in the treatment of autoimmune diseases and the prevention or treatment of rejection in a transplant recipient is disclosed. In addition in vivo and in vitro assays are provided for the assessment and development of drugs capable of suppressing MHC Class I molecules.

5 Claims, 19 Drawing Sheets

OTHER PUBLICATIONS

Bandyopadhyay, et al., "Localization of Gastric Peroxidase and its Inhibition by Mercaptomethylimidazole an Inducer of Gastric Acid Secretion", *Biochem. J.*, 1992, vol. 284, pp. 305–312, month not available.

Davies, et al., "The Influence of Antithyroid Drugs and Iodine on Thyroid Cell MHC Class II Antigen Expression", *Clinical Endocrinology*, 1989, vol. 31, pp. 125–135, month not available.

Elias, et al., "Oral Thioureylene Therapy in Psoriasis—Results in an Open Trial", *Clinical Research*, vol. 41, No. 2, pp. 128A (1993), month not available.

Elias, et al., Methimazole (2–Mercato 1–Methyl Imidazole) in Psoriasis—Results of an Open Trial, Dermatology, vol. 187, pp. 26–29 (1993), month not available.

Faustman, et al., "Prevention of Xenograft Rejection by Masking Donor HLA Class I Antigens", *Science*, 1991, vol. 252, pp. 1700–1702, month not available.

Faustman, et al., "Linkage of Faulty Major Histocompatibility Complex Class I to Autoimmune Diabetes", *Science*, 1991, vol. 254, pp. 1756–1761, month not available.

Hallengreen, et al., "Effects of Antithyroid Drugs on Lymphocyte Function in Vitro", *Journal of Clinical Endocrinology and Metabolism*, 1980, vol. 51, No. 2, pp. 298–301.

Hibbe, et al., "Methimazole Treatment Aggravates Low–Dose Streptozotocin–Induced Diabetes", *Diabetes Research and Clinical Practice*, 1991, vol 11, pp. 53–58, month not available.

Kammüller, et al. "Urinary Biopterin Levels in Mice During Graft–Versus–Host Reactions and During Exposure to 5, 5–Diphenylhydantoin", *Int. J. Immunopharmacology*, 1991, vol. 13, No. 5, pp. 464–473, month not available.

Karlsson, et al., "Immunomodulation by Methimazole Therapy in Graves' Disease: Rapid Changes in Activation Stage of Circulating Regulatory T Cell Subsets, B Cells and NK Cells", *Clin. Exp. Immunol.*, 1988, vol. 74, pp. 258–263, month not available.

Maguire, et al., "In Vivo Function of Regulatory DNA Sequence Elements of a Major Histocompatibility Complex Class I Gene", *Molecular and Cellular Biology*, 1992, vol 12, No. 7, pp. 3078–3086, month not available.

McGregor, et al., "Carbimazole and Autoantibody Synthesis in Hashimoto's Thyroiditis", *British Medical Journal*, 1980, vol. 281, pp. 968–969, month not available.

McLachlan, et al., "The Effect of Carbimazole on Thyroid Autoantibody Synthesis by Thyroid Lymphocytes", *Journal of Clinical Endocrinology and Metabolism*, 1985, vol. 60, No. 6., pp. 1237–1242, month not available.

Morris, "Cyclosporine, FK506 and Other Drugs in Organ Transplantation", *Current Opinion in Immunology*, 1991, vol. 3, pp. 748–751, month not available.

Nogimori, et al., "A New Class of Propylthiouracil Analogs: Comparison of 5'–Deiodinase Inhibition and Antithyroid Activity", *Endocrinology*, 1986, vol. 118, No. 4, pp. 1598–1605, month not available.

Orrego, et al., "Long–Term Treatment of Alcoholic Liver Disease with Propylthiouracil", *The New England Journal of Medicine*, 1987, vol. 317, No. 23, pp. 1421–1427, month not available.

Rennie, et al., "The Influence of Mehtimazole on Thyroglobulin–Induced Autoimmune Thyroiditis in the Rat", *Endocrinology*, 1983, vol. 112, No. 1, pp. 326–330, month not available.

Saji, et al., "Major Histocompatibility Complex Class I Gene Expression in Rat Thyroid Cells is Regulated by Horomones, Methimazole, and Iodide as well as Interferon", *Journal of Clinical Endocrinology and Metabolism*, 1992, vol. 75, No. 3, pp. 871–878, month not available.

Saji, et al., "Hormonal Regulation of Major Histocompatibility Complex Class I Genes in Rat Thyroid FRTL–5 Cells: Thyroid–Stimulating Hormone Induces a Camp–Mediated Decrease in Class I Expression", *Proc. Natl. Acad. Sci. USA*, 1992, vol. 89, pp. 1944–1948, month not available.

Satz, et al., "Structure and Expression of Two Procine Genomic Clones Encoding Class 1 MHC Antigens", *The Journal of Immunology*, 1985, vol. 135, No. 3, pp. 2167, month not available.

Volpe, et al., "Evidence that Antithyroid Drugs Induce Remissions in Graves' Disease by Modulating Thyroid Cellular Activity", *Clinical Endocrinology*, 1986, vol 25, pp. 453–462, month not available.

Waldhäusl, et al., "Immunmodulation Durch Mehtimazol Bei Typ–1 Diabetes", *Akt. Endokrin. Stoffw.*, 1987, vol. 8, pp. 119, month not available.

Weetman, et al., "Methimazole Inhibits Thyroid Autoantibody Production by an Action on Accessory Cells", *Clinical Immunology and Immunopathology*, 1983, vol. 28, pp. 39–45, month not available.

Weetman, "How Antithyroid Drugs Work in Graves' Disease", *Clinical Endocrinology*, 1992, vol. 37, pp. 317–318, month not available.

Weissman, et al., "A Complex Regulatory DNA Element Associated with a Major Histocompatibility Complex Class I Gene Consists of both a Silencer and an Enhancer", *Molecular and Cellular Biology*, 1991, vol. 11, No. 8, pp. 4217–4227, month not available.

Wilson, et al., "The Effect of Antithyroid Drugs on B and T Cell Activity in Vitro", *Clinical Endocrinology*, 1988, vol. 28, pp. 389–397, month not available.

Wilson, et al., "The Effects of Antithyroid Drugs on Intercellular Mediators", *Acta Endocrinologica (Copenh)*, 1990, vol. 122, pp. 605–609. Month not available.

Yoshikawa, et al., "Hyperglucagonemia of Insulin Autoimmune Syndrome Induced by Methimazole in a Patient with Graves' Disease", *Endocrinol. Japon*, 1989, vol. 36, No. 1, pp. 125–134, month not available.

Zelman, et al., "Antithyroid Drugs Interact with Renal Medullary Prostaglandin H Synthase", *J. Lab. Clin. Med.*, 1984, vol. 104, No. 2, pp. 185–192, month not available.

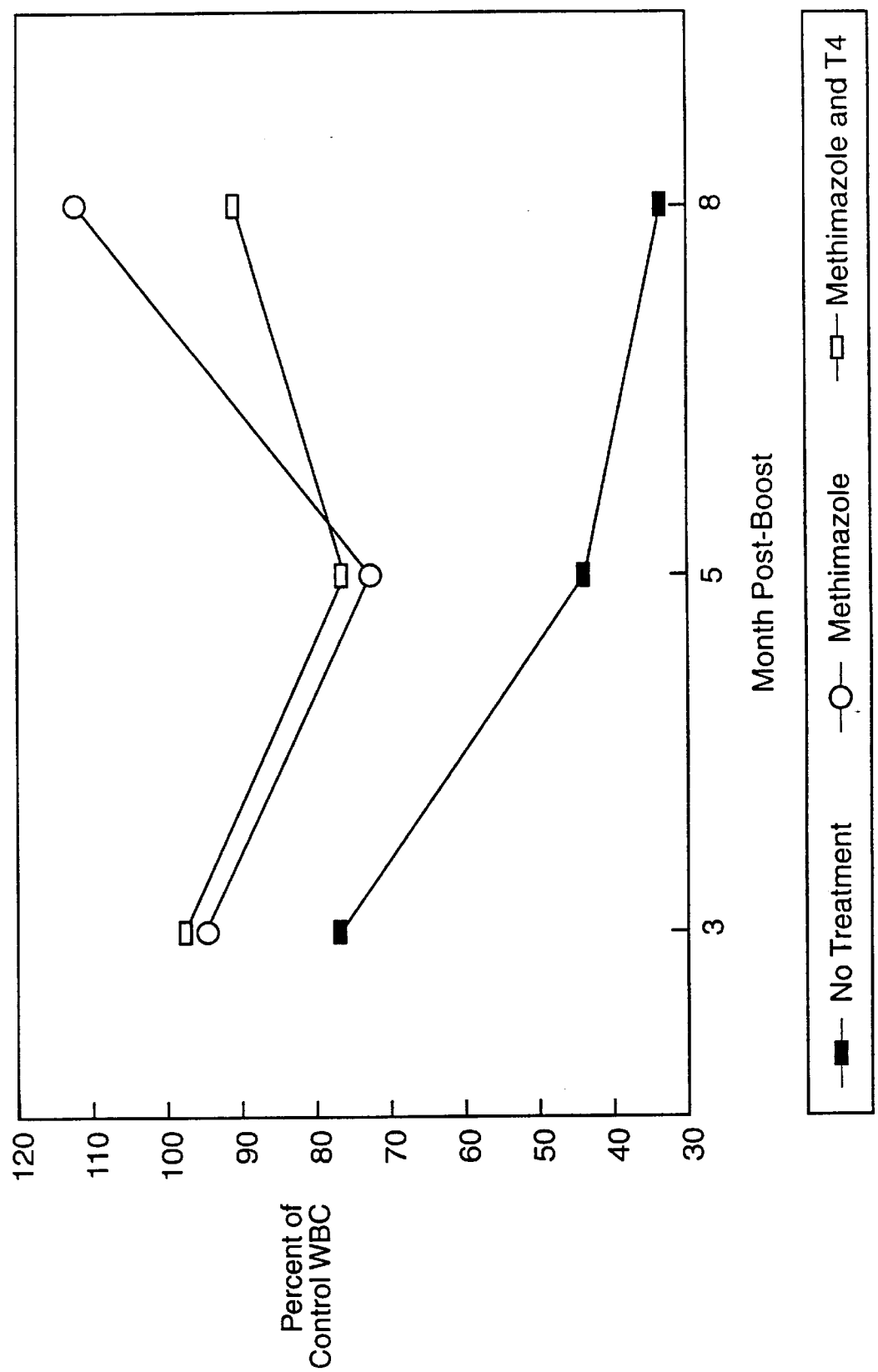

FIG. 9A

```
                                                              PD1
                                                              PROMOTER
     |         |         |         |         |
AAGCTTATCTTTCCTAATTACCATTCTTCAATCCATACTTTAATAGTATT 50
     |         |         |         |         |
GTCTCTGAGGACGTAGGAAGTACATATGAAACACTCCTGCTACCTTCCAA 100
     |         |         |         |         |
AGTACTGTGTCCCAAGGAAAATCATTCTGTGAGCTGCACTAGCCTCTTTT 150
     |         |         |         |         |
TCATGGAATACAACCTTTACTGGAAAGAATGAATGACACTGGAAGATCTA 200
     |         |         |         |         |
TATAACTTAGTGAAACAATGTATTCGGTCTTAAAACTCTTACATTAGTAT 250
     |         |         |         |         |
AAGCAACAGTCAATGTGCAAGCCAGGCTTTTAATTTAACAGAATAGGAAA 300
     |         |         |         |         |
CACGGAGTATACTGATTCAGTCCACATTCAAAATAACCTTTGAGAAATT  350
     |         |         |         |         |
ACCATTATGATAGCATCCAAAATTATCTGAAAAGGTTATTAAAAATACAT 400
     |         |         |         |         |
GTCCTACATGTGTGCGGGGCTTTTACATTTCATAGATGTCAGCCACCAAA 450
     |         |         |         |         |
AGGACTCAGCACAGAAGCAGACATAAACCTCCAGTGGTTTTCCCATGAGC 500
     |         |         |         |         |
CAGACAGCAGAGAGACTTGCCATAGAGTAAAATGTAAAAGCTCCACTCT  550
     |         |         |         |         |
TCACACTACAGTGTTTCTTATGCGAAATAATTGTTTTCATATGAAATGCA 600
     |         |         |         |         |
TGGATTATTTATATCTTCTAAAAATTTGATGAAATTTTAAACTATTATTT 650
     |         |         |         |         |
CTAGTATAGAAAATATCCACTGACGTATCAACACAAACATATCTTAGAGG 700
     |         |         |         |         |
TCTTCACTAATTTGTAAAACTGTAGGAATATTCTCACTAAAAGGTTTGGA 750
     |         |         |         |         |
AATCGCTGGGTACACAGCCCCTGGGCCACTGGAGGCACTGGAGACACTGT 800
     |         |         |         |         |
GACAAAGAGCTTTCTGAAGAGCAGCAGGGCAGAGTCCCAGCTCCGCAGCC 850
     |         |         |         |         |
AGGCGTGGCTCTCAGGGTCTCAGGCTCCAGGGCGGAGTCTGGGCGGGGAG 900
     |         |         |         |         |
```

FIG. 9B

```
                                                              PD1
                                                           PROMOTER
     |           |           |           |
GCGCGGTGGTGGGGAGTCCCCGTGTCCCCAGTTTCACTTCTCCGTCTCGC          950
     |           |           |           |
AACCTGTGTGGGACCGTCCTGCCCGGACACTCGTGACGCGACCCCACTTC         1000
     |           |           |           |
TCTCTCCTATTGCGTGTCCGGTTTCTGGAGAAGCCAATCGGCGCCACTGC         1050
     |           |           |           |
GGTTCCCGGTTCTAAACTCTCCACCCACCCGGCTCTGCTCAGCTTCTCCC         1100
     |           |           |           |
CAGACTCCGAGGCTGAGGATCATGGGGCCTGGAGCCCTCTTCCTGCTGCT         1150
                             MetGlyProGlyAlaLeuPheLeuLeuLe
GTCGGGAACCTTGGCCCTGACCGGCACCAAGGCGGGTGAGTGCGGGATCG         1200
uSerGlyThrLeuAlaLeuThrGlyThrLysAlaGly
GGAACAAGGCCGCTGCGGGGAGGAGCTGAGGCACCGCCTGGGAGTCGGGT         1250
     |           |           |           |
GGGGGCAGGACCCACGGGGAAGGTGCGACTCTGCTGTCCCGGCCCAGACC         1300
     |           |           |           |
CGCCACCTCACCCCGTCCTGTCCTGTCCCTCCCTTGCTTCCTGCTCCTCT         1350
     |           |           |           |
GCTTTTCCCCCCTAAACCCGGGGCCCGTCTCCGACCTCCACCCCTTTCCC         1400
     |           |           |           |
GCCTCCCGAGCCCCGAGCT                                        1450
```

FIG. 11

```
                     ----CATATGAAATG--CATGGA---------TTATTTATATCTTCTAA     34
105  TGAAACAATGTATTCGGTCTAAAA-CTCTTACATTAGTATAAGCAACAGT                    49
114  GTCCACATTCAAAATAACCTTTGAGAAATTACCATAATGATAGCATCCAA                    50
140                 **···*···      ·****·*··**·

AAATT-------GATGAAATTTAAACTATTATTCTAGTATA---GAA                       74
105  CAATGTGCAAGCCAGGCTTTTAATTTAACAGAA-------TAGGAAACACGG                  94
114  -AATTATCTGAAAAGGTTATTAAAAATACATGTCCTACATGTGTGCGGGG                    99
140         TTF-2        ··*·······*·······

AATATCCA---CTGACGTATCAAC-ACAAACATATC                                 106
105  AGTATACTGAT-------TCAG-----------                                    109
114  CTTTTACATTTCATAGATGTCAGCCCACCAAAAGGAC                                135
140       ·*·* *.                    ***·
```

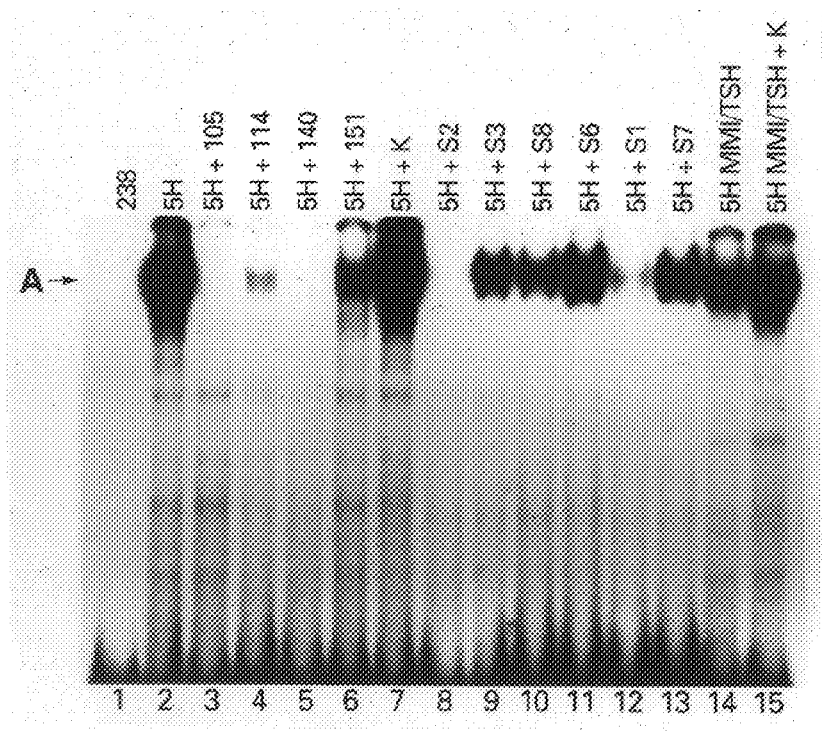
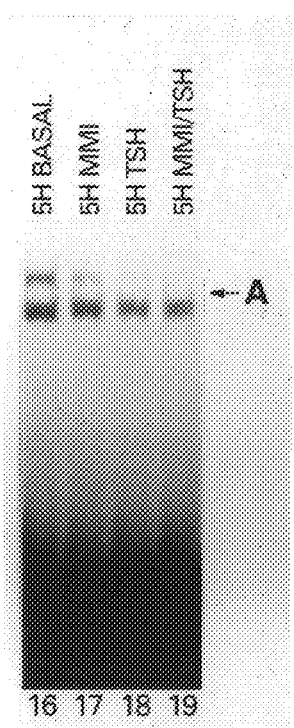

METHODS OF TREATING AUTOIMMUNE DISEASES AND TRANSPLANTATION REJECTION

This is a divisional of application Ser. No. 08/073,830 filed Jun. 7, 1993, now abandoned.

FIELD OF THE INVENTION

This invention is in the field of treatment of autoimmune diseases and transplantation rejection in a mammal. More specifically, this invention relates to methods for treating and preventing these diseases using drugs capable of suppressing expression of the major histocompatibility complex (MHC) Class I molecules and to methods for the development or assessment of drugs that are capable of suppressing MHC Class I expression.

BACKGROUND OF THE INVENTION

A primary function of the immune response is to discriminate self from non-self antigens and to eliminate the latter. The immune response involves complex cell to cell interactions and depends primarily on three major cell types: thymus derived (T) lymphocytes, bone marrow derived (B) lymphocytes, and macrophages. The immune response is mediated by molecules encoded by the major histocompatibility complex (MHC). The two principal classes of MHC molecules, Class I and Class II, each comprise a set of cell surface glycoproteins ("Basic and Clinical Immunology" (1991) Stites, D. P. and Terr, A. I. (eds), Appelton and Lange, Norwalk, Conn./San Mateo, Calif.). MHC Class I molecules are found on virtually all somatic cell types, although at different levels in different cell types. In contrast, MHC Class II molecules are normally expressed only on a few cell types, such as lymphocytes, macrophages and dendritic cells.

Antigens are presented to the immune system in the context of Class I or Class II cell surface molecules; $CD4^+$ helper T-lymphocytes recognize antigens in association with Class II MHC molecules, and $CD8^+$ cytotoxic lymphocytes (CTL) recognize antigens in association with Class I gene products. It is currently believed that MHC Class I molecules function primarily as the targets of the cellular immune response, whereas the Class II molecules regulate both the humoral and cellular immune response (Klein, J. and Gutze, E., (1977) "Major Histocompatibility Complex" Springer Verlag, N.Y.; Roitt, I. M. (1984) Triangle, (Engl Ed) 23:67–76; Unanue, E. R. (1984) Ann. Rev. Immunology, 2:295–428). MHC Class I and Class II molecules have been the focus of much study with respect to research in autoimmune diseases because of their roles as mediators or initiators of the immune response. MHC-Class II antigens have been the primary focus of research in the etiology of autoimmune diseases, whereas MHC-Class I has historically been the focus of research in transplantation rejection.

Graves' disease is a relatively common autoimmune disorder of the thyroid. In Graves' disease, autoantibodies against thyroid antigens, particularly the thyrotropin receptor, alter thyroid function and result in hyperthyroidism ("Basic and Clinical Immunology" (1991) Stites, D. P. and Terr, A. I. (eds), Appelton and Lange, Norwalk, Conn./San Mateo, Calif.: pages 469–470). Thyrocytes from patients with Graves' disease have aberrant MHC-Class II expression and elevated MHC Class I expression. (Kohn et al., (1992) In "International Reviews of Immunology," Vol. 912:135–165).

Thionamide therapy has historically been used to treat Graves' disease. The most commonly used thionamides are methimazole (MMI), carbimazole (CBZ) and propylthiouracil (PTU). These thionamides contain a thiourea group; the most potent are thioureylenes (W. L. Green (1991) In Werner and Ingbar's "The Thyroid: A Fundamental Clinical Text" 6th edition, L. Braverman and R. Utiger (eds), J. B. Lippincott Co. page 324). The thionamides restore a euthyroid state by inhibiting thyroid peroxidase catalyzed formation of the thyroid hormones produced by the thyroid stimulating autoantibody stimulated thyroid (Solomon, D. H. (1986) In "Treatment of Graves' Hyperthyroidism". Ingbar, S. H., Braverman, L. E. (eds) The Thyroid: J B Lippincott Co., Philadelphia, Pa., p. 987–1014; Cooper, D. S. (1984) N. Engl. J. Med., 311: 1353–1362; Cooper, D. S. (1991) Treatment Of Thyrotoxicosis. In Werner And Ingbar's "The Thyroid: A Fundamental and Clinical Text," 6th edition. L. Braverman and R. Utiger (eds), J. B. Lippincott Co. pages 887–916). It has been reported that MMI and PTU can inhibit peroxidase-dependent enzymes in the kidney and that MMI can inhibit gastric peroxidase in rat gastric mucosa (Zelman, S. J. et al., (1984) J. Lab. Clin. Med. 104:185–192; Bandyopadhyay, U. et al., (1992) Biochem J. 284:305–312). PTU has also been reported to inhibit hepatoxicity associated with alcoholism (Orrego, H. et al., (1987) N. Engl. J. of Med. 317:1421–1427). Thionamides have been used to treat Graves' patients for extended periods of time with the majority of patients experiencing no complication related to this therapy (Cooper, D. S. (1991) Treatment Of Thyrotoxicosis. In Werner And Ingbar's "The Thyroid: A Fundamental and Clinical Text," 6th edition. L. Braverman and R. Utiger (eds), J. B. Lippincott Co. pages 887–916). Allergic reactions, including such symptoms as fever, rash, urticaria, occur in 1–5% of patients. Toxic reactions to thionmide treatments are rare, occurring in only 0.2 to 0.5% of the patients (Cooper, D. S. (1991) Treatment Of Thyrotoxicosis. In Werner And Ingbar's "The Thyroid: A Fundamental and Clinical Text," 6th edition. L. Braverman and R. Utiger (eds), J. B. Lippincott Co. pages 887–916).

In addition to the effect of thionamides on thyroid hormone synthesis, it was recognized that thionamide therapy in Graves' disease was associated with a reduction in thyroid autoantibodies (Cooper, D. S. (1982) N. Clin. Endocrinol. Metab. 29:231–238; Kuzuya, N. et al., J. Clin. Endocrinol. Metab. 48:706–714; Bech, K. and Madsen, S. N. (1980) Clin Endocrinol (Oxf) 13:417–26; Hallengren, B. et al. (1980) J. Clin. Endocrinol. Metab 51:298–301; Cooper, D. S. (1991) Treatment Of Thyrotoxicosis. In Werner And Ingbar's "The Thyroid: A Fundamental and Clinical Text," 6th edition. L. Braverman and R. Utiger (eds), J. B. Lippincott Co. pages 887–916). Studies on the mechanism by which thionamides exert this effect are contradictory. One hypothesis suggests that the thionamides act directly on thyroid follicular cells and that the subsequent modulation in thyroid activity results in the immune effects (Volpe et al., (1986) Clin. Endocrinol. 25:453–462). A second hypothesis suggests that thionamides act directly on lymphocytes, particularly thyroid lymphocytes (Weetman, A. P. (1992) Clin Endocrinol. 37:317–318; McGregor, A. M. (1980) Brit. Med. J., 281:968–969). It has also been suggested that MMI interferes with antigen handling by accessory cells because these cells possess a peroxidase enzyme system (Weetman, A. P. (1983) Clin. Immuno. and Immunopath, 28:39–45). The current consensus appears to be that the therapeutic action of the thionamides, including the immunosuppressive effects, is thyroid specific and intrathyroidal (D. S. Cooper (1991) Treatment Of Thyrotoxicosis. In Werner And Ingbar's "The Thyroid: A Fundamental and Clinical Text," 6th edition. L. Braverman and R. Utiger (eds), J. B. Lippincott Co. pages 888–889).

Results of studies involving the use of MMI in the treatment of diabetes are also contradictory. Hibbe, T. et al., (1991); *Diabetes Res. and Clin. Practice* 11:53–58, report that MMI enhances the development of streptozotocin-mediated diabetes in mice. In contrast, Waldhausl, W. et al. (1987) Akt. Endokrin. Stoffw. 8, 119 (abstract) report enhanced remission in 54% of 11 patients treated with MMI shortly after diagnosis of type I diabetes, basing their therapy on reputed effects of MMI on T helper cells. These authors reported no change in the levels of Class I and Class II antigens and it is unclear whether the effect was due to MMI or natural remission of the disease over the 9 month "honeymoon" period. In the BB rat, MMI depressed spontaneous development of thyroiditis but did not reduce the incidence of diabetes (Allen, F. M. et al., (1986)*Am. J. Med. Sci.*, 292:267–271; Braverman, L. E. et al., (1987) *Acta. Endocrinol.* (Coppenhagen) Suppl. 281:70–76).

Saji, M. et al. (1992a); *Proc. Natl. Acad. Sci. U.S.A.* 89:1944–1948 describe hormonal regulation of MHC-class I genes in the rat thyroid cell line, FRTL-5. Treatment of the FRTL-5 cell line with thyroid stimulating hormone (TSH) resulted in decreased transcription of MHC class I DNA and reduced cell surface levels of MHC Class I antigens. Recently, a report by Saji, M. et al., (1992b) *J. Clin. Endocrinol. Metab.* 75:871–878, demonstrated that agents such as serum, insulin, insulin-like growth factor-I (IGF-1), hydrocortisone and thyroid stimulating thyrotropin receptor autoantibodies from Graves' patients decrease MHC-Class I gene expression in that FRTL-5 cells. In addition, treatment of the FRTL-5 cells with MMI or high doses of iodide resulted in decreased MHC Class I gene expression. The effect of MMI on reduction of MHC Class I expression was shown to be at the level of transcription and was additive with thyroid stimulating hormone and other hormones which normally suppress Class I in these cells. Saji, M. et al. (1992b) *J. Clin. Endocrinol. Metab.* 75:871–878, suggest a new mechanism by which MMI may act in the thyroid during treatment of Graves' disease; no extrapolation was made to any other autoimmune diseases. Prior to these studies it was known that Rous sarcoma virus, adenoviruses 12 and 2 and certain Gross viruses reduced expression of MHC Class I; however, SV40, Rad LV, and Mo MuLV viruses can increase Class I MHC expression (Singer & Maguire (1990) *Crit. Rev. in Immun.* 10:235–257).

Systemic lupus erythematosus (SLE) is a chronic autoimmune disease that, like Graves', has a relatively high rate of occurrence. SLE affects predominantly women, the incidence being 1 in 700 among women between the ages of twenty and sixty ("Cellular and Molecular Immunology" (1991) Abbus, A. K., Lichtman, A. H., Pober, J. S. (eds); W. B. Saunders Company, Philadelphia: page 360–370). SLE is characterized by formation of a variety of autoantibodies and by multiple organ system involvement ("Basic and Clinical Immunology" (1991) Stites, D. P. and Terr, A. I. (eds), Appelton and Lange, Norwalk, Conn./San Mateo, Calif.: pages 438–443). Current therapies for treating SLE involve the use of corticosteroids and cytotoxic drugs, such as cyclosporin. Immunosuppressive drugs such as cyclosporin, FK506, or rapamycin suppress the immune system by reducing T cell numbers and function (Morris, P. J. (1991) *Curr. Opin. in Immun.*, 3:748–751). While these immunosuppressive therapies alleviate the symptoms of SLE, and other autoimmune diseases, they have numerous severe side effects. In fact, extended therapy with these agents may cause greater morbidity than the underlying disease.

Women suffering from SLE who have breast cancer face particular difficulties. These individuals are immunosuppressed as a result of corticosteroid and cytotoxic drug treatment for SLE; radiotherapy for the treatment of the cancer would additionally enhance the immunosuppressed state. Further, radiation therapy, a current method of choice can exacerbate disease expression or induce severe radiation complications. For these individuals, alternative therapies that would allow for simultaneous treatment of SLE and the cancer are greatly needed.

As is true for autoimmune diseases, there is a great need for different ways of treating or preventing transplantation rejection. Transplantation rejection occurs as a result of histoincompatibility between the host and donor; it is the major obstacle in successful transplantation of tissues. Current treatment for transplantation rejection, as for autoimmune disease, involves the use of a variety of immunosuppressive drugs and corticosteroid treatment.

Faustman et al., (PCT International Application No. 92/04033 published Mar. 19, 1992) identify a method for inhibiting rejection of a transplanted tissue in a recipient animal by modifying, eliminating, or masking the antigens present on the surface of the transplanted tissue. Specifically, this application suggests modifying, masking, or eliminating human leukocyte antigen (HLA) Class I antigens. The preferred masking or modifying drugs are F(ab)' fragments of antibodies directed against HLA-Class I antigens. However, the effectiveness of such a therapy will be limited by the hosts' immune response to the antibody serving as the masking or modifying agent. In addition, in organ transplantation this treatment would not affect all of the cells because of the perfusion limitations of the masking antibodies. Faustman et al. disclose that fragments or whole viruses be transfected into donor cells, prior to transplantation into the host, to suppress HLA Class I expression. Use of whole or fragments of virus presents potential complications to the recipient of such transplanted tissue since some viruses, SV40 in particular, can increase Class I expression (Singer and Maguire (1990) *Crit. Rev In Immunol.* 10:235–237, TABLE 2).

Durant et al. (British Patent No. 592, 453 Published Jul. 9, 1981) identify isothiourea compositions that may be useful in the treatment of autoimmune diseases and host versus graft (HVG) disease and assays for assessing the immunosuppressive capabilities of these compounds. However, this study does not describe MMI or the suppression of MHC Class I molecules in the treatment of autoimmune diseases.

U.S. Pat. Nos. 5,010,092 and 5,097,441 describe a method for reducing nephrotoxicity resulting from administration of an antibiotic in a mammal by coadministration of the antibiotic with either MMI or CBZ. These patents neither suggest nor teach the use of MMI to suppress MHC Class I expression in the treatment of autoimmune diseases or in the treatment and prevention of transplantation rejection.

SUMMARY OF THE INVENTION

This invention relates to methods for treating autoimmune diseases in mammals and for preventing or treating transplantation rejection in a transplant recipient. These methods involve administering to a mammal in need of treatment a drug capable of suppressing expression of MHC Class I molecules. This invention also relates to pretreating transplantable cells, tissues or organs prior to transplantation into a recipient with a drug capable of suppressing MHC Class I molecules. In particular this invention relates to the use of MMI in treating autoimmune diseases in mammals and for preventing or treating transplantation rejection in a transplant recipient.

This invention further includes methods for in vivo and in vitro assays for the development and assessment of drugs capable of suppressing expression of MHC Class I molecules.

One in vivo method is comprised of three steps. First, MHC Class I deficient mice are used to evaluate the importance of MHC Class I in a particular experimental autoimmune disease. Second, an animal which is useful as a model for a particular autoimmune disease, either experimentally induced or spontaneous, is exposed to the drug being evaluated. Third, the therapeutic potential of the drug is evaluated by the alleviation of symptoms or signs of the autoimmune disease in the treated animal.

Another in vivo method is also comprised of three steps. First, a mammalian cell line, tissue or organ is treated with the drug. Second, the treated cells, tissues, or organs are transplanted into a mammal which may also be treated with the drug. Third, the cells are removed from the recipient mammal and cell survival is evaluated.

There are two methods for the in vitro assays. In the first method the ability of the drug to suppress expression of MHC Class I molecules is assessed by treating mammalian cells with a candidate drug, combining cell extracts from the treated cells with MHC Class I regulatory nucleic acid sequences, detecting formation of a complex between the nucleic acid sequences and proteins from the extract, and comparing alterations in complex formation in extracts from treated and untreated cells. In the second in vitro method, the therapeutic potential of the drug is evaluated by its ability to down regulate Class I transcription in cells, as assessed by reporter gene assays.

An object of the invention is to provide a method for treating mammals suffering from autoimmune diseases.

Another object of the invention is to provide a method of preventing or treating rejection of a tissue in a transplant recipient.

A further object of the invention is to provide a method for preventing rejection of cells containing a recombinant gene transplanted into a mammal in need of gene therapy.

Another object of the invention is to provide in vivo and in vitro assays for the assessment and development of drugs capable of suppressing MHC Class I molecules.

A further object of the invention is to provide in vivo and in vitro assays that are predictive of the therapeutic usefulness of candidate drugs.

1A. Titration of 16/6Id binding in the sera of immunized mice; purified 16/6Id immobilized on plates.

1B. Titration of single-stranded DNA binding in the sera of immunized mice; single-stranded DNA immobilized on plates.

1C. Titration of nuclear antigen binding in the sera of immunized mice; nuclear extract immobilized on plates.

1D. Titration of ovalbumin binding in the sera of immunized Class I-deficient mice (●); ovalbumin immobilized on plates. Sera of Class I-deficient mice which were not immunized with ovalbumin (○) are the control in this experiment.

FIGS. 2A–2D show that Class I-deficient mice do not respond to immunization with monoclonal anti-16/6Id antibody. Serial two-fold dilutions of sera were analyzed by ELISA, 7 weeks after immunization. Results are the average of measurements of 6 animals. Standard deviation value did not exceed 10% of the mean. Sera of anti-16/6Id-immunized control 129 (■) and anti-16/6Id-immunized class I-deficient mice (●)

2A. Titration of anti-16/6Id binding in the sera of immunized mice; purified rabbit polygonal anti-16/6Id immunoglobulin immobilized on plates.

2B. Titration of single-stranded DNA binding in the sera of immunized mice; single-stranded DNA immobilized on plates.

2C. Titration of 16/6Id binding in the sera of immunized mice; 16/6Id immobilized on plate.

2D. Titration of nuclear antigens binding in the sera of immunized mice; nuclear extract immobilized on plate.

Figure 3A:
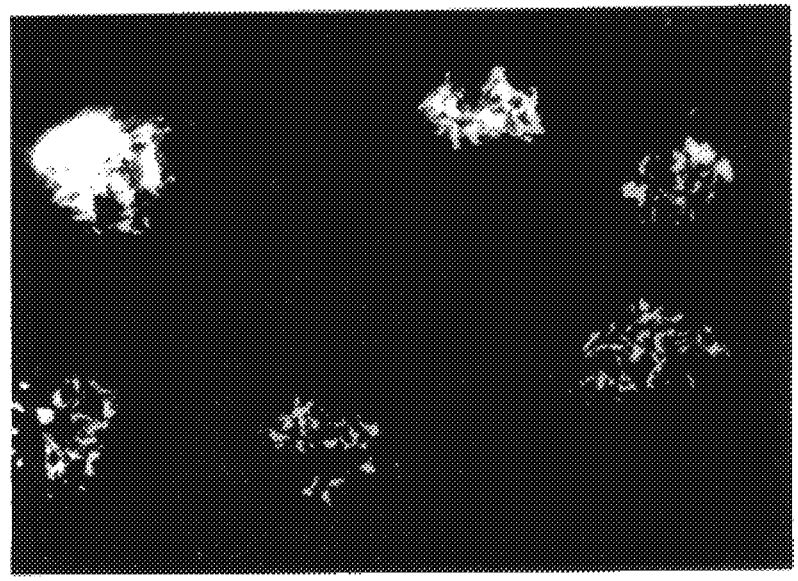
Figure 3B:
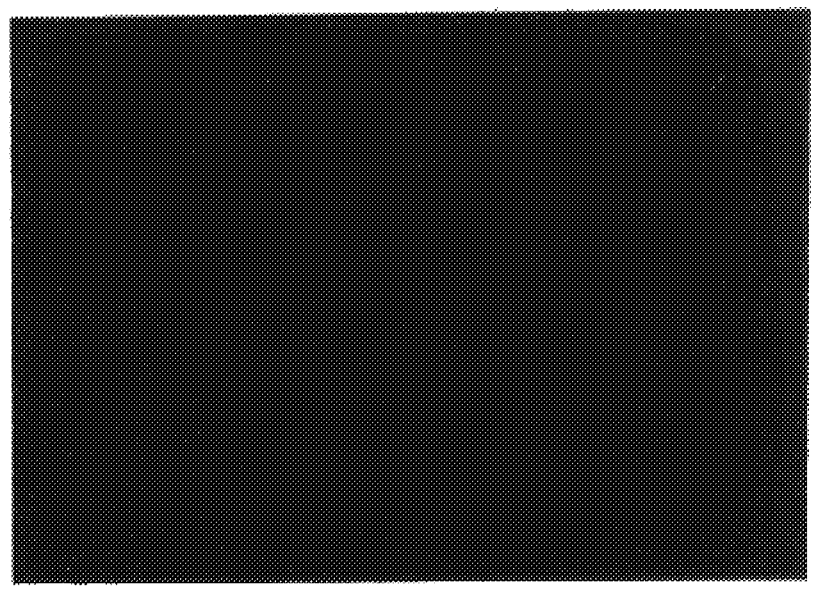

FIGS. 3A–3B shows immunohistological examination of kidney sections of Class I-deficient (FIG. 3B) and control 129 (FIG. 3A) mice injected with 16/6Id. Frozen kidney sections (5 μm thick) were fixed and stained with FITC-conjugated, gamma chain-specific goat anti-mouse IgG (magnification X200). The kidney sections shown are from one individual in each group and are representative of that group.

Figure 4A:
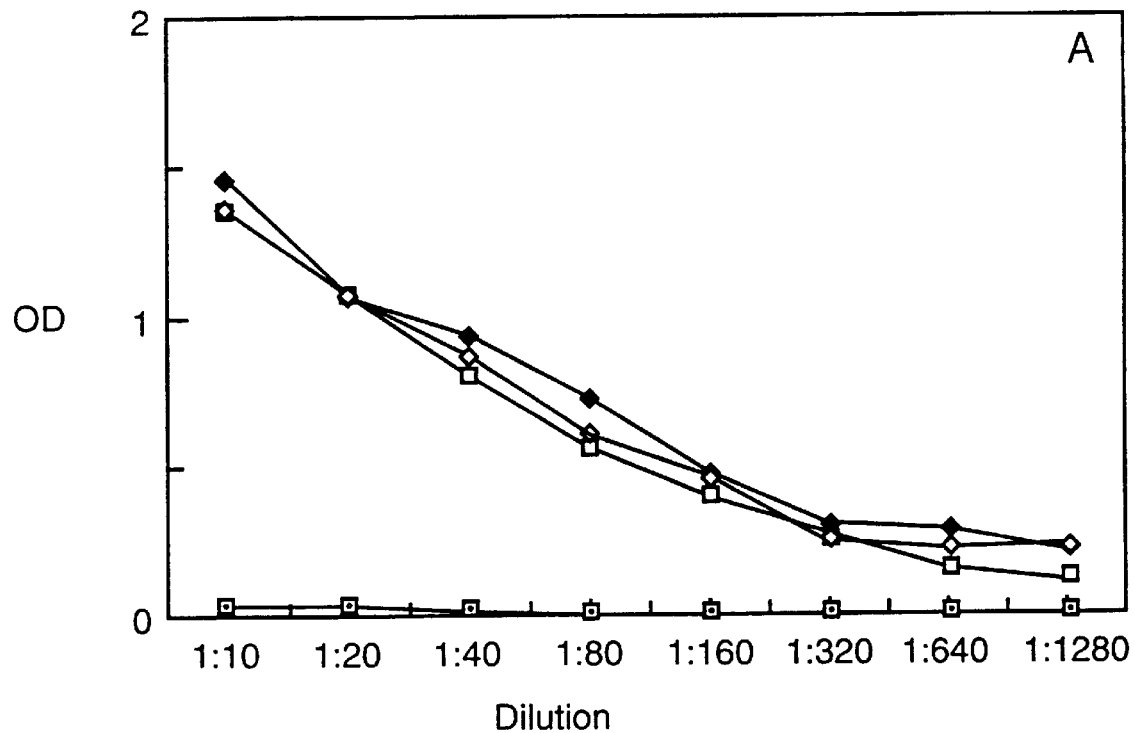
Figure 4B:
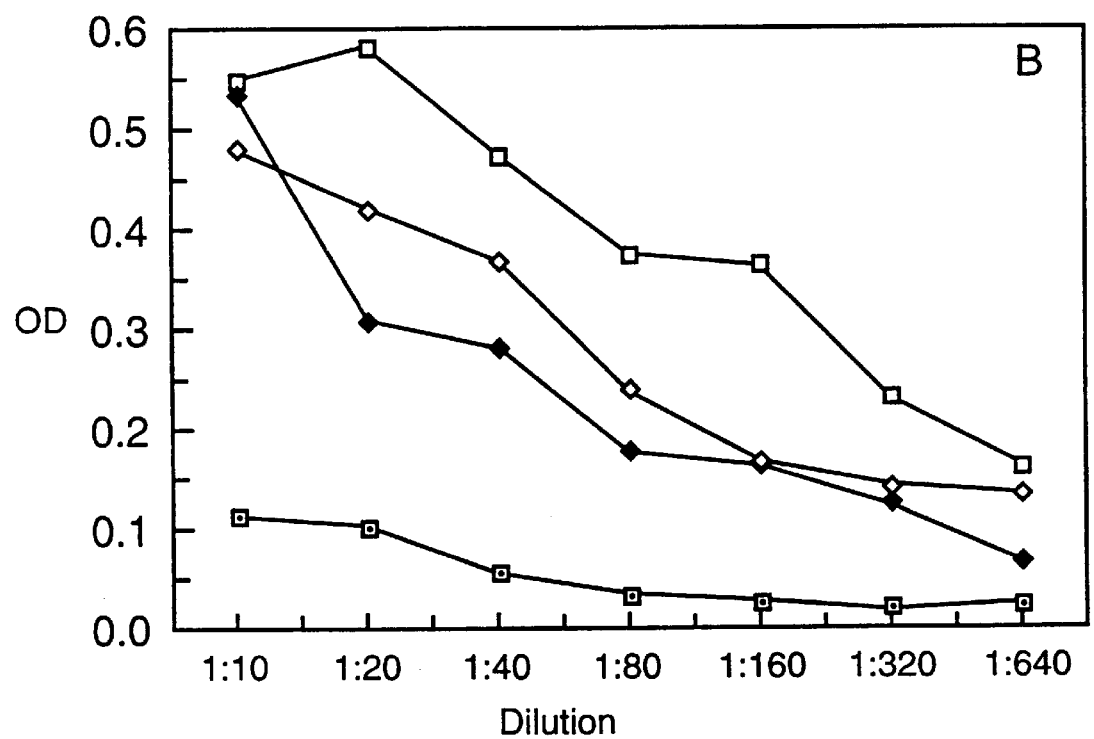
Figure 4C:
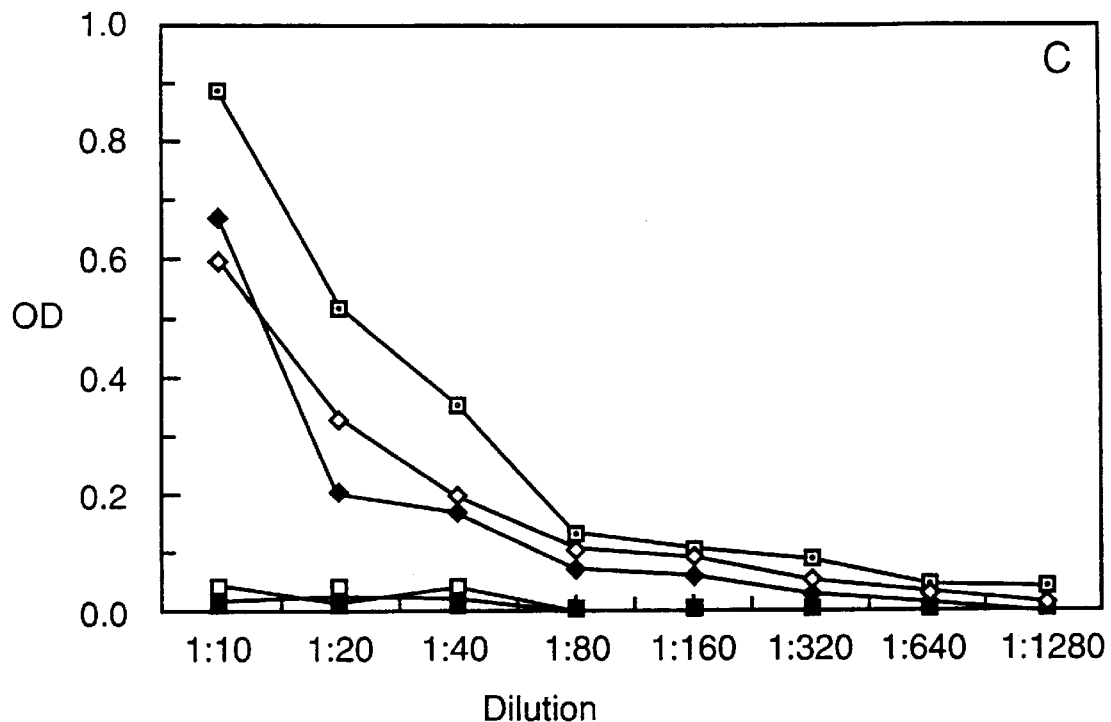
Figure 4D:
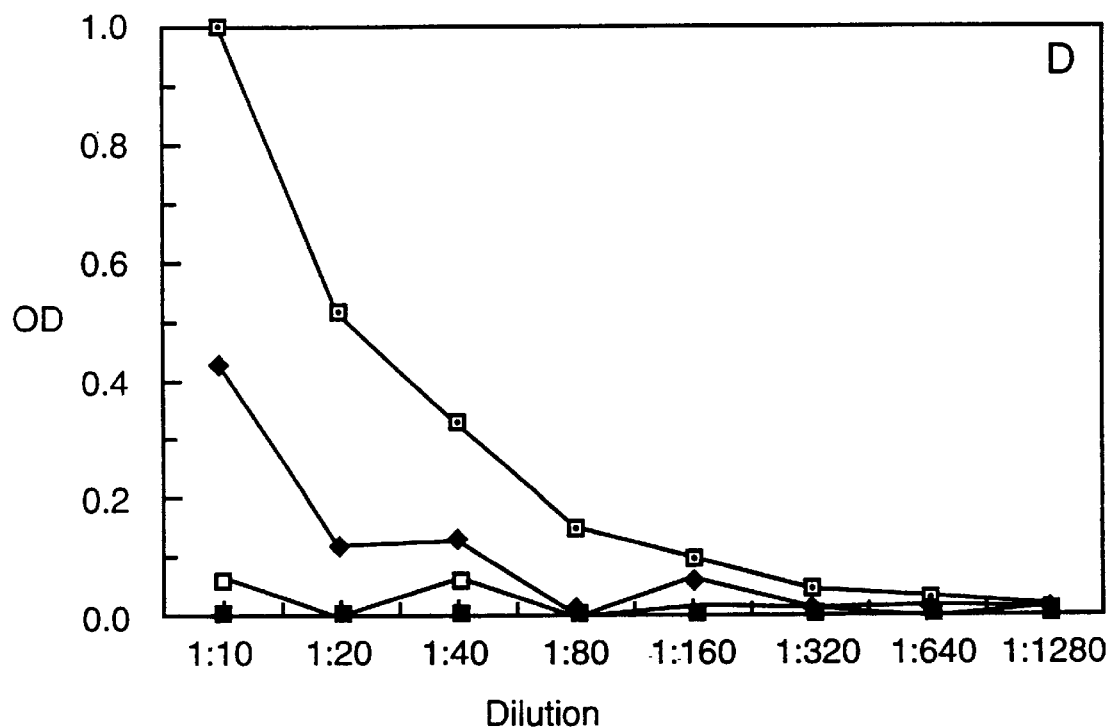

FIGS. 4A–4D. FIGS. 4A and 4B show the appearance of anti-16/6Id and anti-DNA antibodies in mice exposed to a single immunization and boost with a human monoclonal anti-DNA antibody bearing the 16/6Id. FIGS. 4C and 4D show titers of the anti-16/6Id and anti-DNA antibodies in mice after treatment with MMI.

4A. Shows the titer of anti-16/6Id antibodies in mice prior to treatment with MMI. Control Balb/c mice which received no immunization (■); 16/6Id immunized mice which will or will not be treated with MMI or MMI plus thyroid hormone, specifically thyroxine (T$_4$) (◇, ♦, □).

4B. Shows the titer of anti-DNA antibodies in mice prior to treatment with MMI. Designations are the same as in (A).

4C. Shows the titer of anti 16/6Id antibodies in mice after treatment with MMI or MMI and thyroxine (T$_4$). Control animals immunized with 16/6Id but receiving no treatment (■); animals immunized with 16/6Id then treated with 60 days of MMI (♦), or with 60 days of MMI and T$_4$ (◇); animals which were not immunized with 16/6Id but were treated with 60 days of MMI (■) or animals treated with 60 days of MMI and T$_4$ (□).

4D. Shows the titer of anti DNA antibodies in mice after treatment with MMI or MMI and thyroxine (T$_4$). Designations are the same as in (C).

FIG. 5 shows the relative white blood cell (WBC) count as a percentage of the WBC in 16/6Id-treated control animals with no exposure to MMI or thyroxine (T$_4$) (■); in 16/6Id-treated animals exposed to MMI(○); and 16/6Id-treated animals exposed to MMI and T$_4$(□) at 3 months, 5 months and 8 months after the boost.

Figure 6A:
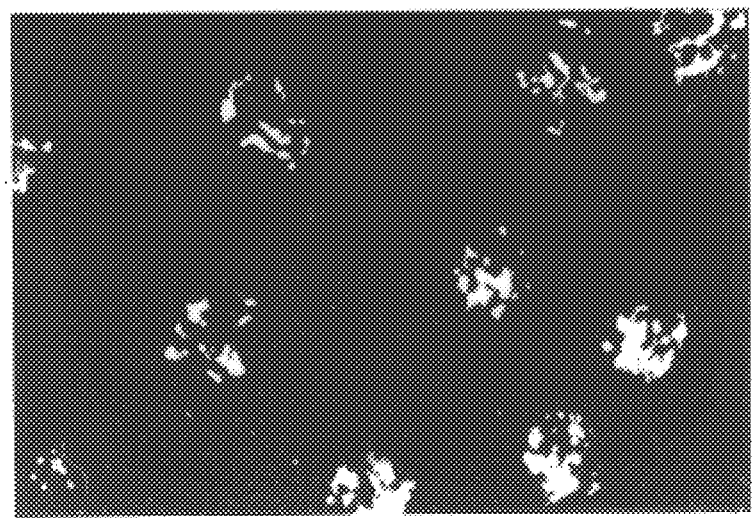
Figure 6B:
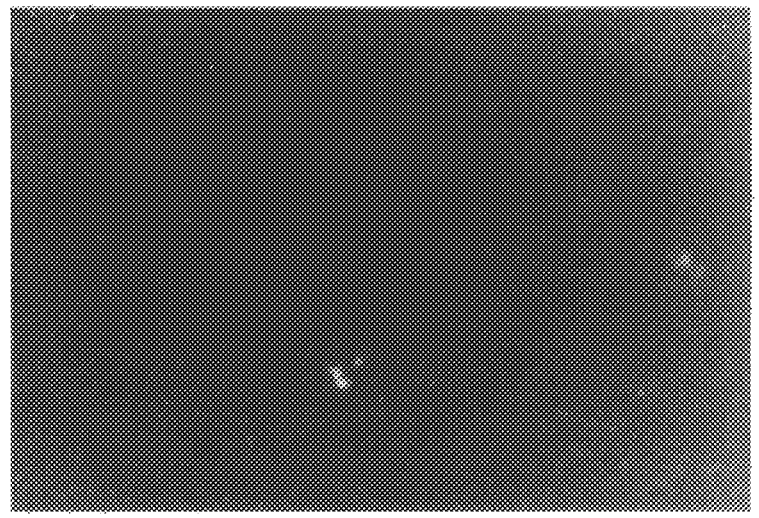

FIGS. 6A–6B shows the development of immune complexes in the kidneys of 16/6Id-treated mice treated with MMI (FIG. 6B) versus 16/6Id-treated animals not treated with MMI (FIG. 6A).

FIGS. 7 A–D shows the effect of MMI treatment on lymphocyte populations during experimental SLE disease. The experimental SLE disease resulted from treatment with 16/6Id.

7A. Shows the distribution of the lymphocyte populations in mice immunized with 16/6Id (▨); mice immunized with 16/6Id and treated with MMI and thyroxine (T$_4$) (■); mice immunized with 16/6Id and treated with T$_4$ (▨); mice immunized with 16/6Id and treated with MMI (▨); and mice immunized with 16/6Id and administered placebo (▨).

7B. Shows the levels of Class I on T cells over time in mice immunized with 16/6Id (▨) and mice immunized with 16/6Id and treated with MMI (■).

7C. Shows the levels of Class I on B cells over time in mice immunized with 16/6Id (▨) and mice immunized with 16/6Id and treated with MMI (■).

7D. Shows the levels of Class II on B cells over time in mice immunized with 16/6Id (▨) and mice immunized with 16/6Id and treated with MMI (■).

Figure 8:
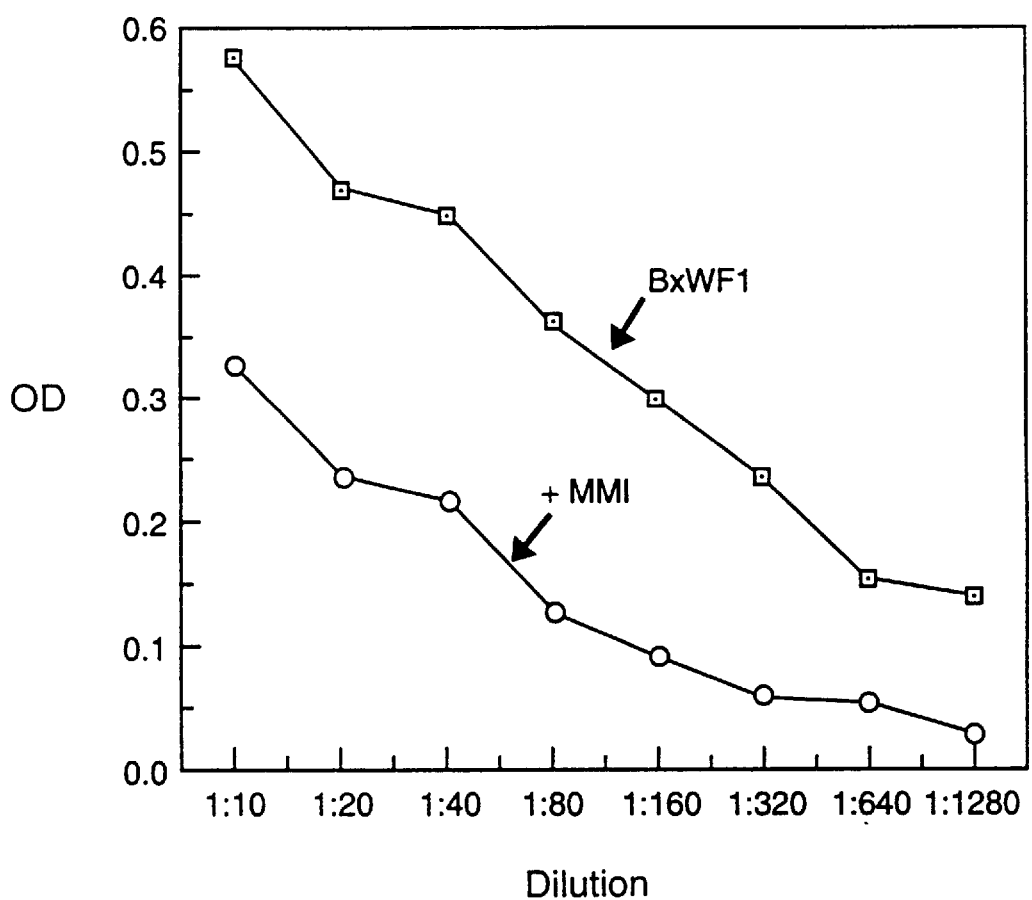

FIG. 8 shows the effect of 2 months of MMI treatment (15 mg released over 30 days by pellet implantation) on anti-DNA antibody titers in NZBxNZWF1 mice. Control animals (BxWF1) (●) and BxWF1 animals treated with MMI (○). NZBxNZWF1 mice are a mouse model of SLE that develop spontaneous SLE.

FIGS. 9A–9B shows the sequence of PD1 promoter with the 151 (bold), 114 (bold and underlined), 140 (bold and boxed) and 238 (bold and wavy box) regions or fragments of the 5' portion of the PD1 promoter. The 238 region includes an AT rich 105 region (underlined). The ATG start site is noted by the amino acid 3 letter code starting with Met. The numbers at the right indicate the number of base pairs counting from the first nucleotide in the uppermost line.

Figure 10:
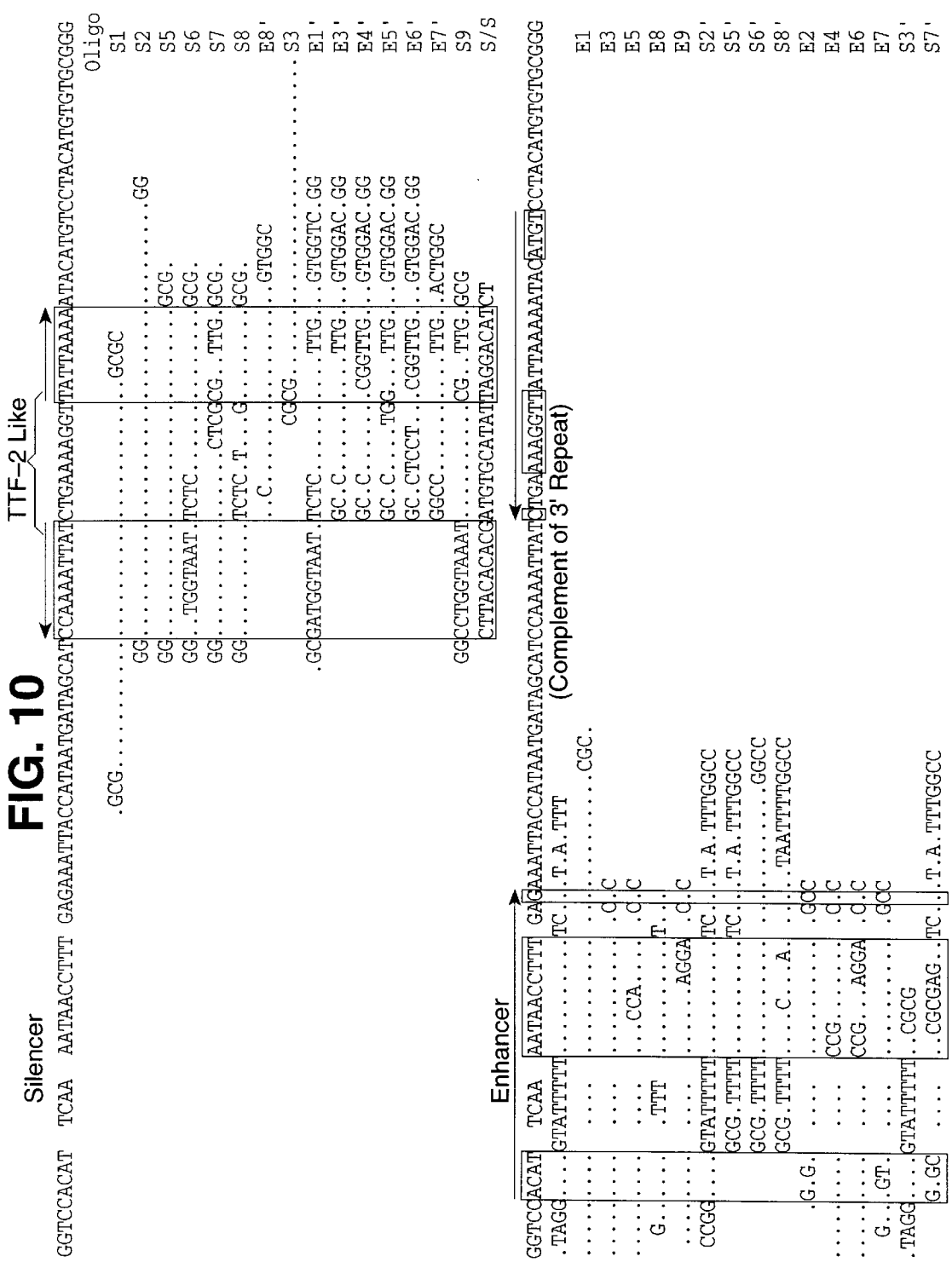

FIG. 10 shows the silencer and enhancer regions of the 140 fragment with oligonucleotides used to map the region for activity in gel mobility shift assays. The silencer region which is relevant to the MMI effects on complex formation in mobility gel shift assay is noted by the opposites arrows separated by a thyroid transcription factor-2 (TTF-2)-like binding element which is insulin-sensitive. Mapping of silencer- and enhancer-binding sites was by inhibition of complex formation by various double-stranded (ds)-oligonucleotides. A series of ds-oligonucleotides spanning the 140-bp AvaII-DdeI DNA fragment was tested for the ability to compete against enhancer and silencer complexes. Of these, the only ones that competed were those contained within the 96-bp segment shown. To determine important residues for binding, variant ds-oligonucleotides were synthesized and tested for their abilities to inhibit silencer and enhancer complex formation. Boxed regions represent sequences determined by the inhibition studies using the ds-oligonucleotides to be critical for complex formation, dots denote residues identical to the native sequence. For simplicity, only one strand of the ds-oligonucleotide sequence used in competition studies is shown.

FIG. 10 (top) shows oligonucleotides used to map the silencer-binding site. Arrows delineate boundaries to the silencer element. FIG. 10 (bottom) shows oligonucleotides used to map the enhancer-binding site. Arrows delineate the interrupted, inverted repeat of the enhancer.

FIG. 11 shows the alignment of the 114 fragment, 140 fragment and 105 fragment of the 238 fragment to show sequence homology. The silencer region is outlined in 140 by the arrows as in FIG. 10. All respond to MMI, as does 151. Also identified, as in FIG. 10, is the TTF-2 like sequence. The (*) denotes identity with the 140 fragment; the (●) homology with the 140 fragment in at least one other fragment; the (--) denote gaps inserted by the computer to derive the best fit. On the right, the numbers denote the residue in each fragment which is defined in FIG. 9 when each is sequentially numbered starting with number one.

FIGS. 12 A–D show mobility-shift assays using the radiolabelled 140, 114 and 151 fragments noted in FIG. 9 and cell extracts from FRTL-5 rat thyroid cells. Cell extracts from treated or untreated FRTL-5 cells were incubated with the radiolabelled DNA fragments, and resulting DNA fragment-protein complexes were electrophoresed in a polyacrylamide gel and visualized by autoradiography. The complex affected by MMI is denoted A.

12A. Shows the gel mobility shift assays of the 140 radiolabelled fragment: lane 1 contains the 140 radiolabelled fragment alone; lane 2 contains cell extracts from FRTL-5 rat thyroid cells maintained in the presence of 6H medium and treated with MMI; lane 3 contains cell extracts from FRTL-5 rat thyroid cells maintained in the presence of 6H medium and not treated with MMI; lane 4 contains cell extracts from FRTL-5 rat thyroid cells maintained in the presence of the 5H medium; lane 5 contains cell extracts from FRTL-5 rat thyroid cells maintained in the presence of 5H medium and treated with MMI; lane 6 contains cell extracts from FRTL-5 rat thyroid cells maintained in the presence of 5H medium and treated with thyroid stimulating hormone (TSH); and lane 7 contains cell extracts from FRTL-5 rat thyroid cells maintained in 5H medium and treated with MMI and TSH.

12B. Shows the gel mobility shift assays of the 114 radiolabelled fragment with FRTL-5 rat thyroid cell extracts. Lane 1 contains the 114 radiolabelled fragment alone; lane 2 contains cell extracts from FRTL-5 rat thyroid cells maintained in the presence of 6H medium and treated with MMI; lane 3 contains cell extracts from FRTL-5 rat thyroid cells maintained in the presence of 6H medium and not treated with MMI; lane 4 contains cell extracts from FRTL-5 rat thyroid cells maintained in the presence of the 5H medium; lane 5 contains cell extracts from FRTL-5 rat thyroid cells maintained in the presence of 5H medium and treated with MMI; lane 6 contains cell extracts from FRTL-5 rat thyroid cells maintained in the presence of 5H medium and treated with thyroid stimulating hormone (TSH); and lane 7 contains cell extracts from FRTL-5 rat thyroid cells maintained in 5H medium and treated with MMI and TSH.

Figure 12A:
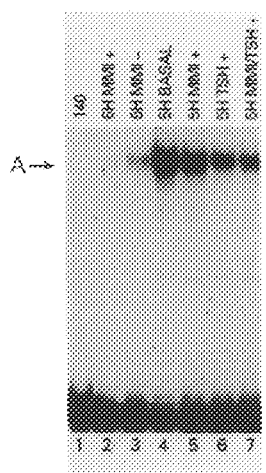
Figure 12B:
Figure 12C:
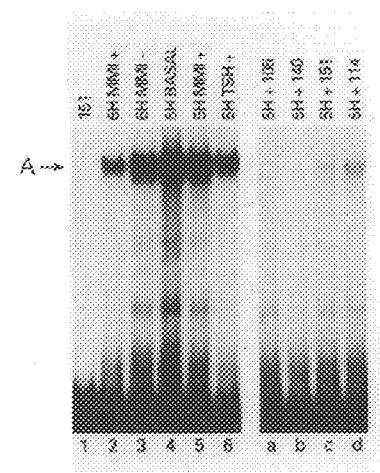
Figure 12D:
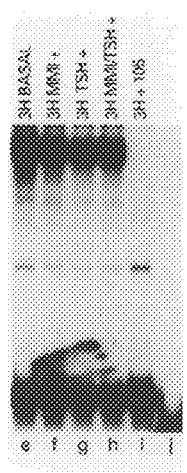

12C. Shows the gel mobility shift assays of the 151 radiolabelled fragment with FRTL-5 cell extracts. Lane 1 contains the 151 radiolabelled fragment alone; lane 2 contains cell extracts from FRTL-5 rat thyroid cells maintained in the presence of 6H media and treated with MMI; lane 3 contains cell extracts from FRTL-5 rat thyroid cells maintained in the presence of 6H medium and not treated with MMI; lane 4 contains cell extracts from FRTL-5 rat thyroid cells maintained in the presence of the 5H medium; lane 5 contains cell extracts from FRTL-5 rat thyroid cells maintained in the presence of 5H medium and treated with MMI; lane 6 contains extracts from FRTL-5 rat thyroid cells maintained in the presence of 5H medium and thyroid stimulating hormone (TSH). Lanes a–d in FIG. 12C shows the formation of the A complex in the gel shift mobility assays of the 151 radiolabelled fragment plus FRTL-5 cell extracts can be competed by unlabelled 105, 140, 151 and 114 fragments. The incubation mixture in lane (a) contains the 151 radiolabelled fragment, cell extracts from FRTL-5 rat thyroid cells maintained in the presence of 5H medium, and unlabelled 105 fragment; lane (b) contains the 151 radiolabelled fragment, cell extracts from FRTL-5 rat thyroid cells maintained in the presence of 5H medium, and unlabelled 140 fragment; lane (c) contains the 151 radiolabelled fragment, cell extracts from FRTL-5 rat thyroid cells maintained in the presence of 5H medium, and unlabelled 151 fragment; lane (d) contains the radiolabelled 151 fragment, cell extracts from FRTL-5 rat thyroid cells maintained in the presence of 5H medium and unlabelled 114 fragment.

12D. Shows the gel mobility shift assays of the radiolabelled-140 fragment with extracts from treated and untreated FRTL-5 cell maintained in 3H medium. Unlike 5H medium, 3H medium contains no insulin. The incubation in lane (j) contains the 140 radiolabelled fragment alone; lane (e) contains cell extracts from FRTL-5 rat thyroid cells maintained in the presence of 3H medium; lane (f) contains cell extracts from FRTL-5 rat thyroid cells maintained in 3H medium and treated with MMI; lane (g) contains cell extracts from FRTL-5 rat thyroid cells maintained in the presence of 3H medium and treated with TSH; lane (h) contains cell extracts from FRTL-5 rat thyroid cells maintained in the presence of 3H medium and treated with MMI and TSH; lane (i) contains unlabelled 105 fragment together with cell extracts from FRTL-5 rat thyroid cells maintained in the presence of 3H medium.

Figure 13:
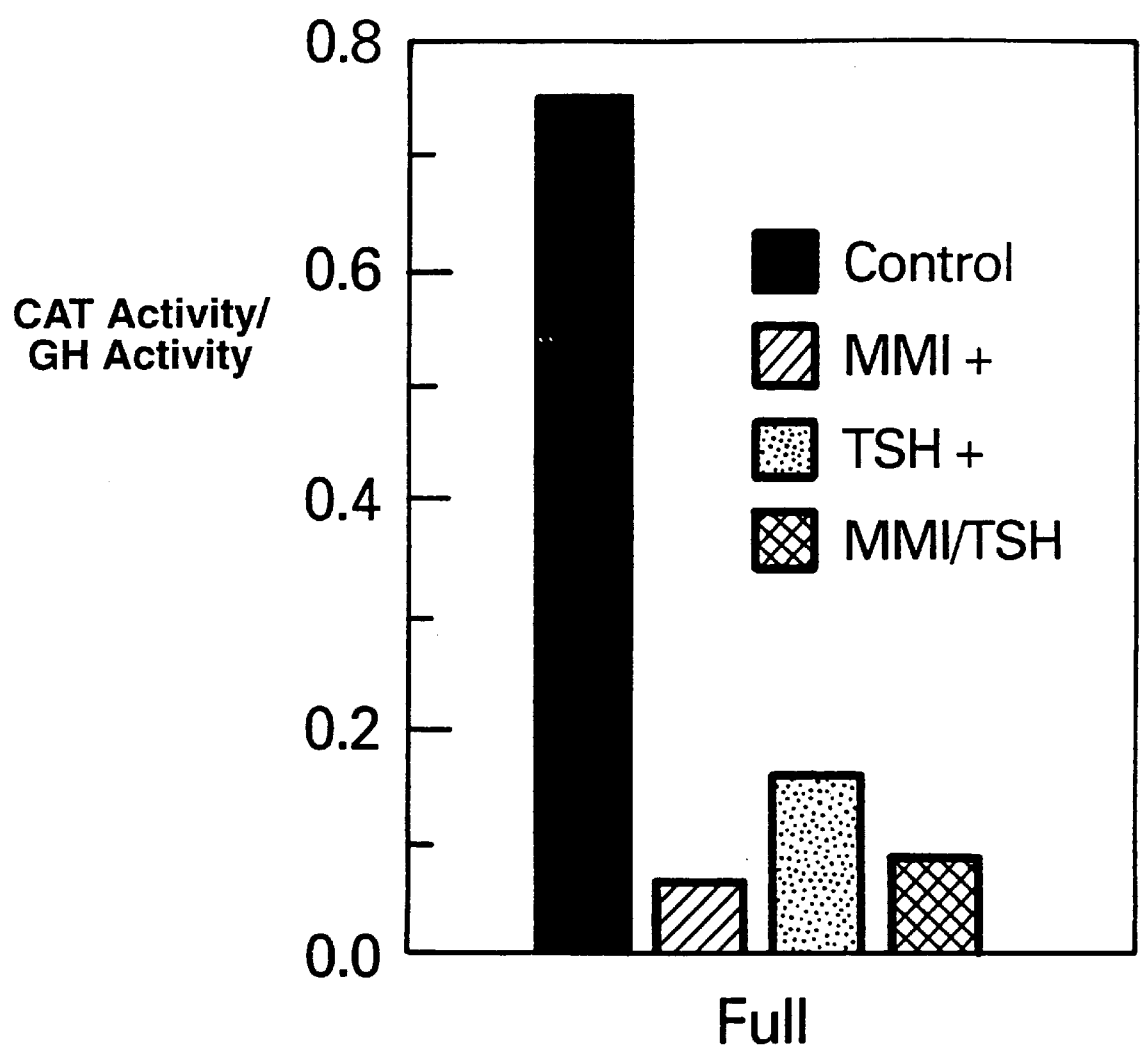

FIG. 13 shows transfection data with chloramphenicol acetyltransferase (CAT) chimeras showing that MMI inhibits full length MHC Class I PD1 promoter activity. FRTL-5 rat thyroid cells were transfected with the full length PD1 promoter, CAT chimeric construct and the cells either received no treatments (■), treatment with MMI (▨), treatment with TSH (▨) or treatment with TSH and MMI (▩).

FIGS. 14A–B shows the gel shift mobility assays of the radiolabelled 238 fragment (FIG. 14(A)) or the radiolabelled K oligonucleotide (FIG. 14(B)) with extracts from treated or untreated FRTL-5 rat thyroid cells maintained in 5H medium. The complex affected by MMI is denoted by A.

14A. Shows the gel mobility shift assays of the radiolabelled 238 fragment incubated with extracts from treated or untreated rat thyroid FRTL-5 cells maintained in 5H medium and with unlabelled double-stranded (ds) oligonucleotides shown in FIG. 10. The incubation in lane 1 contains the 238 radiolabelled fragment alone; lane 2 contains cell extracts from FRTL-5 rat thyroid cells maintained in the presence of 5H medium and not treated with MMI; lane 3 contains cell extracts from FRTL-5 rat thyroid cells maintained in the presence of 5H medium and unlabelled 105 fragment; lane 4 contains cell extracts from FRTL-5 rat thyroid cells maintained in the presence of the 5H medium and unlabelled 114 fragment; lane 5 contains cell extracts from FRTL-5 rat thyroid cells maintained in the presence of 5H medium and unlabelled 140 fragment; lane 6 contains cell extracts from FRTL-5 rat thyroid cells maintained in the presence of 5H medium and unlabelled 151 fragment; lane 7 contains cell extracts from FRTL-5 rat thyroid cells maintained in 5H medium and unlabelled K-oligonucleotide; lane 8 contains cell extracts from FRTL-5 rat thyroid cells maintained in the presence of 5H medium and unlabelled ds-oligonucleotide S2 (shown in FIG. 10); lane 9 contains cell extracts from FRTL-5 rat thyroid cells maintained in the presence of 5H medium and unlabelled ds-oligonucleotide S3 (shown in FIG. 10); lane 10 contains cell extracts from FRTL-5 rat thyroid cells maintained in the presence of 5H medium and unlabelled ds-oligonucleotide S8 (shown in FIG. 10); lane 11 contains cell extracts from FRTL-5 rat thyroid cells maintained in the presence of 5H medium and unlabelled ds-oligonucleotide S6 (shown in FIG. 10); lane 12 contains cell extracts from FRTL-5 rat thyroid cells maintained in the presence of 5H medium and unlabelled ds-oligonucleotide S1 (shown in FIG. 10); lane 13 contains cell extracts from FRTL-5 rat thyroid cells maintained in the presence of 5H medium and unlabelled ds-oligonucleotide S7 (shown in FIG. 10); lane 14 contains cell extracts from FRTL-5 rat thyroid cells maintained in the presence of 5H medium and treated with MMI and TSH; lane 15 contains unlabelled K-oligonucleotide plus cell extracts from FRTL-5 rat thyroid cells maintained in the presence of 5H medium and treated with MMI and TSH.

14B. Shows the gel mobility shift assays of radiolabelled K-oligonucleotide incubated with extracts from treated or untreated rat thyroid cells maintained in 5H medium. In lane 16, the incubation contains the radiolabelled K oligonucleotide with cell extracts from FRTL-5 rat thyroid cells maintained in the presence of 5H medium alone. In lane 17 the incubation contains radiolabelled K oligonucleotide with cell extracts from FRTL-5 rat thyroid cells maintained in the presence of 5H medium and treated with MMI; lane 18 contains the radiolabelled K oligonucleotide with cell extracts from FRTL-5 rat thyroid cells maintained in the presence of the 5H medium and treated with TSH; lane 19 contains the radiolabelled K oligonucleotide and cell extracts from FRTL-5 rat thyroid cells maintained in the presence of 5H medium and treated with MMI and TSH.

DETAILED DESCRIPTION OF THE INVENTION

For the purpose of a more complete understanding of the invention the following definitions are described herein. Mammal includes, but is not limited to, humans monkeys, dogs, cats, mice, rats, hamsters, cows, pigs, horses, sheep and goats. Drug includes, but is not limited to, MMI, MMI derivatives, CBZ, PTU, thioureylenes, and thionamides. Other candidate drugs include aminothiazole, 1,1,3-tricyano-2-amino-1-propene, phenazone, thioureas, thiourea derivatives, goitrin derivatives, thiouracil derivatives, sulfonamides, aniline derivatives, derivatives of perchloric acid, iodide, thiocynanates, carbutamide, para-aminobenzoic acid, para-aminosalicylic acid, amphenone B, resorcinol, phloroglucinol, and 2-4-dihydrobenzoic acid, all of which have been noted to have goitrinogen activity and suppress thyroid function. One skilled in the art will also understand that other drugs may be developed by the in vivo and in vitro assays described in examples 2, 3, 4, 5, 6 and 7. These drugs may be natural, synthetic or recombinant in origin. By a drug capable of suppressing expression of MHC Class I molecules we mean a drug that has the capability of decreasing or abolishing MHC Class I cell surface molecules on mammalian cells treated with the drug relative to mammalian cells not treated with the drug. Major histocompatibility complex (MHC) is a generic designation meant to encompass the histocompatibility antigen systems described in different species, including the human leukocyte antigens (HLA). Tissue, includes, but is not limited to, single cells, cells, whole organs and portions thereof. Transplantation rejection includes, but is not limited to, graft versus host disease and host versus graft disease. Autoimmune disease includes, but is not limited to, autoimmune dysfunctions and autoimmune disorders.

This invention provides a method for treating autoimmune disease and for preventing or treating rejection of a tissue in a transplant recipient. More specifically this invention relates to methods for administering to a mammal in need of such treatment a drug or drugs capable of suppressing expression of MHC Class I molecules.

Examples of autoimmune diseases that can be treated by this method include, but are not limited to, rheumatoid arthritis, psoriasis, juvenile diabetes, primary idiopathic myxedema, systemic lupus erythematosus, De Quervains thyroiditis, thyroiditis, autoimmune asthma, myasthenia gravis, scleroderma, chronic hepatitis, Addison's disease, hypogonadism, pernicious anemia, vitiligo, alopecia areata, Coeliac disease, autoimmune enteropathy syndrome, idiopathic thrombocytic purpura, acquired splenic atrophy, idiopathic diabetes insipidus, infertility due to antispermatazoan antibodies, sudden hearing loss, sensoneural hearing loss, Sjogren's Syndrome, polymyositis, autoimmune demyelinating diseases such as multiple sclerosis, transverse myelitis, ataxic sclerosis, pemphigus, progressive systemic sclerosis, dermatomyositis, polyarteritis nodosa, chronic hepatitis, hemolytic anemia, progressive systemic sclerosis, glomerular nephritis and idiopathic facial paralysis. Preferred drugs for treating autoimmune diseases by this method are MMI, MMI derivatives, CBZ, and PTU.

In a preferred embodiment, the MHC Class I suppressing drug MMI is administered to a mammal, preferably a human, afflicted with an autoimmune disease. Suitable therapeutic amounts of MMI are in range of 0.01 mg-500 mg per day. A preferred dosage is 0.1 mg–100 mg per day and a more preferable dosage is 2.5–50 mg per day. Suitable therapeutic amounts of CBZ are in the same range as MMI. The dosage can be administered daily, in approximately equally divided amounts at 8-hour intervals or with breakfast, lunch and dinner. The preferred maintenance dose for adult is 5–15 mg per day for periods of up to one year. Therapy can be continuous, for example 2.5–30 mg per day for periods up to one year. Alternatively, therapy can be tapered, for example, 50–100 mg per day at the start, tapering to 5–10 mg per day within 4 to 10 weeks according to thyroid hormone (thyroxin ($T_4$) or triiodothyronine ($T_3$)) or thyroid stimulating hormone (TSH) levels in an individual receiving such treatment. Alternatively PTU is administered to a mammal, preferably a human, afflicted with an autoimmune disease. Suitable therapeutic amounts of PTU are in the range 0.1 mg–2000 mg per day. A preferred dosage for PTU is in a range ten-fold higher than the dosage ranges described above for MMI. The preferred maintenance dose of MMI for children is 0.4 mg per kg, divided into three daily doses at eight hour intervals initially, then half the initial dose to maintain as preferred. It is understood by one skilled in the art that the dosage administered to a mammal afflicted with an autoimmune disease may vary depending on the mammals age, severity of the disease and response to the course of treatment. One skilled in the art will know the clinical parameters to evaluate to determine proper dosage for an afflicted mammal.

In another preferred embodiment, MMI is administered to a mammal, preferably a human, afflicted with systemic lupus erythematosus (SLE). A preferred therapeutic amount is in the range of 2.5–50 mg per day, administered over 6–12 months, but can be administered in discontinuous treatment periods of similar length over a five year period or for as long as necessary. Alternatively, MMI may be administered in conjunction with the current therapies for SLE, hydrocortisone and cytotoxic drugs, to suppress the disease. SLE patients with breast cancer cannot be readily treated with radiotherapy since they are already immunosuppressed by the ongoing treatment for SLE. Also SLE may be associated with unusual sensitivity to radiation complications therefore radiotherapy exacerbates the disease. It is anticipated that use of MMI to treat SLE individuals with breast cancer will allow radiotherapy to be administered to such individuals without exacerbation of their condition or the radiation complications.

In another embodiment, a MHC Class I suppressing drug is administered to a mammal, preferably a human, afflicted with an autoimmune disease associated with the development of thyroid autoantibodies in the sera of these animals.

In another embodiment, a MHC Class I suppressing drug is administered to a mammal, preferably a human, afflicted with an autoimmune disease characterized by the development of receptor autoantibodies. For example, autoimmune asthma is associated with β-adrenergic receptor autoantibodies. Treatment with a MHC Class I suppressing drug, preferably MMI, will alleviate the disease. Another example of such an autoimmune disease is Myasthenia Gravis. Myasthenia Gravis is associated with acetylcholine receptor autoantibodies. Individuals afflicted with myasthenia gravis have a higher frequency of thyroid autoimmunity. Because of the structural and functional relationship between the TSH and acetylcholine receptors, treatment of an animal, preferably a human, afflicted with Myasthenia Gravis with a MHC Class I suppressing drug will help suppress the disease.

The MHC Locus in all mammalian species contains numerous genes and is highly polymorphic. In humans the HLA Complex contains the HLA-A, HLA-B and HLA-C genes which encode Class I HIA molecules and the HLA-DR, HLA-DQ and HLA-DP genes which encode the Class II molecules. Different HLA molecules bind different antigens. Specific HLA antigens have been associated with a predisposition to a particular disease. For example, Ankylosing spondylitis is associated with HLA-B27, rheumatoid arthritis with HLA-DR4 and insulin-dependent diabetes mellitus with HLA-DR3 and, HLA-DR4. ("Basic and Clinical Immunology" (1991) Stites, D. P. and Terr, A. I. (eds), Appelton and Lange, Norwalk, Conn./San Mateo, Calif.). In contrast, insulin-dependent diabetes mellitus is negatively associated with HLA-DR2 ("Basic and Clinical Immunology" (1991) Stites, D. P. and Terr, A. I. (eds), Appelton and Lange, Norwalk, Conn./San Mateo, Calif.).

Individuals who are HLA-B35 negative, a Class I haplotype, are at low risk of developing scleroderma. Among individuals who develop scleroderma and are HLA-B35 positive, 80% will develop thyroid autoimmune disease and/or will develop thyroid antibodies. In addition, these individuals, are particularly susceptible to human immunodeficiency virus (HIV) infection with rapid disease progression (Kaplan, C et al., (1990) *Hum. Hered* 40:290–298; Cruse, J. M. et al., (1991) *Pathology,* 59:324–328; Itescu, S. et al., (1991) *J. of Accuired Immune Deficiency Syndrome* 5: 37–45; Scorza, R. et al., (1988) *Human Immunology* 22:73–79). MHC Class I suppressing drugs should mitigate the symptoms not only of scleroderma but also mitigate progression of HIV, allowing for a better prognosis for these individuals. In a preferred embodiment the MHC Class I suppressing drug used to treat individuals afflicted with HIV is MMI. A preferred therapeutic amount is in the range of 5–50 mg per day.

In another embodiment, MMI is administered to a mammal, preferably a human, afflicted with an autoimmune disease as an adjunct therapy in the treatment of an autoimmune disease. For example, De Quervains thyroiditis is currently treated with hydrocortisone or salicylates; it is anticipated that the addition of MMI plus hydrocortisone or salicylates will more efficiently suppress the disease.

In another embodiment, MMI and thyroid hormone are co-administered to a mammal in need of such treatment so as to compensate for suppression of thyroid hormone production by MMI. The thyroid hormones thyroxin ($T_4$) or triiodothyronine. ($T_3$) may be co-administered with MMI; thyroxin co-administered with MMI is preferable. A preferred dose of thyroxin is 0.01 to 0.5 mg per day and a more preferable dosage is 0.1 to 0.3 mg per day.

The method of this invention is also suitable for preventing or treating rejection of a transplanted tissue in a recipient mammal, preferably a human. Examples of tissues which may be transplanted include, but are not limited to, heart, lung, kidney, bone marrow, skin, pancreatic islet cells, thyroid, liver and all endocrine tissues, neural tissue, muscle, fibroblast, and adipocytes.

In a preferred embodiment, pancreatic islet cells are isolated from a donor and treated with MMI prior to transplantation into a recipient suffering from diabetes. Diabetes is caused by loss of islet cells as a result of autoimmune disease. Transplantation of islet cells will correct such a deficiency. Islet cells may be treated with 0.1 to 50 mM MMI. The islet cells are preferably treated with 0.1 to 10 mm MMI, in the form of an aqueous solution for 24 to 72 hours or longer as necessary to suppress expression of MHC Class I molecules on the islet cells. After transplantation the recipient may be further treated with MMI or MMI and hydrocortisone or MMI and immunosuppressive agents.

Tumors of certain tissues can be treated by total destruction of that tissue and associated tumor. For example, thyroid tumors are treated with radioiodine to destroy both normal and diseased tissue to stop the progression of the disease. Continuous cultures of normal human thyroid cells are now available. In another embodiment of this invention, these human cells could be treated with MMI to suppress MHC Class I expression and transplanted into a recipient in need of thyroid cells. This technology would provide human donor cells for transplantation on demand since cells could be maintained in culture, treated with MMI and transplanted into a recipient. Further, these human cells may be from noncogeneic individuals, since suppression of MHC Class I by MMI will reduce the possibility that the immune system of the recipient will recognize these cells as "nonself".

In another embodiment of this invention, whole organs may be pretreated by perfusion with MMI to suppress MHC Class I expression. As a drug of low molecular weight MMI will readily perfuse the organ, cross blood vessel barriers and thereby act on most or all cells in the organ. This would reduce or avoid the need for exact matches of donor and recipient in transplantation.

In another embodiment, post transplantation individuals are treated with MMI and hydrocortisone. Hydrocortisone or hydrocortisone in conjunction with other immunosuppressive agents is currently used as a therapy for individuals after transplantation. Hydrocortisone and other hormones are additive with MMI in their effect on MHC Class I levels. Thus it is anticipated pretreatment with MMI, plus treatment with MMI and hydrocortisone or MMI, hydrocortisone and other immunosuppressive agents after transplantation will reinforce self tolerance.

In another embodiment of this invention, MMI is used to pretreat cells containing a recombinant gene, so that the cells may be transplanted into a mammal, preferably a human in need of gene therapy. To provide gene therapy to an individual, a genetic sequence which encodes a desired protein is inserted into a vector and introduced into a host cell. Examples of diseases that may be suitable for gene therapy include, but are not limited to sickle cell anemia, cystic fibrosis, β-thalassemia, hemophilia A and B, glycosyl transferase enzyme defects, and cancer. Examples of vectors that may be used in gene therapy include, but are not limited to, defective retroviral, adenoviral, or other viral vectors (Mulligan, R. C. (1993) *Science* Vol. 260:926–932). The means by which the vector carrying the gene may be introduced into the cell include, but is not limited to, electroporation, transduction, or transfection using DEAE-dextran, lipofection, calcium phosphate or other procedures known to one skilled in the art (Sambrook, J. et al. (1989) in "Molecular Cloning. A Laboratory Manual", Cold Spring Harbor Press, Plainview, N.Y.).

Examples of cells into which the vector carrying the gene may be introduced include, but are not limited to, continuous cultures of normal human cells, such as human pancreatic islet or thyroid cells or continuous cultures of normal mammalian cells such as rat FRTL-5 cells. In a preferred embodiment, FRTL-5 rat thyroid cells containing a recombinant gene under a thyroid specific promoter are treated with MMI to suppress MHC Class I. The treated cells are transplanted into a mammal, preferably a human, and secrete factors able to control the disease. Such cells can be maintained in prolonged culture, in a functioning growing state and treated with MMI or MMI with hormone supplementation to suppress Class I. Cells carrying a variety of recombinant genes could be readily available on demand. Elimination of the need for autologous cells would allow a major advance in transplantation.

In another embodiment of this invention an in vivo assay is used to assess the ability of a candidate drug to suppress MHC Class I expression. In the first step of the assay, the role of MHC Class I in a particular autoimmune disease is evaluated by determining if the symptoms or signs of that particular autoimmune disease can be induced in MHC Class I-deficient mice. Lack of inducibility of the autoimmune disease in MHC Class I-deficient mice would suggest a role for MHC Class I in that disease. Examples of MHC Class I-deficient mice which can be used include, but are not limited to, MHC Class I-deficient mice generated by homologous recombination, MHC Class I-deficient mice created by insertion of transgenes, and MHC Class I-deficient mice created by chromosomal loss. MHC Class I-deficient mice are also commercially available. Methods by which the autoimmune disease can be recreated in these mice include, but are not limited to, viral infection, induction by antibodies and induction by chemicals or other environmental agents. Alternatively, Class I-deficient animals can be mated with spontaneous autoimmune animal models and the resulting progeny analyzed for autoimmune disease.

In a preferred embodiment MHC Class I deficient mice are immunized with a human monoclonal anti-DNA antibody bearing a major idiotype, designated 16/6Id. (Shoenfeld, Y. et al. (1983) *J. Exp. Med.* 158:718–730). In the next step of this embodiment an animal model of the autoimmune disease is exposed to the MHC Class I suppressing drug. Examples of autoimmune animal models include, but are not limited to, transgenic animals, animals generated by homologous recombination, chromosomal loss and animals with naturally or spontaneously occurring disease.

In a preferred embodiment, SLE is experimentally induced in mice. Examples of how SLE is experimentally induced in mice include, but are not limited to, immunization with a monoclonal 16/6 idiotype (Shoenfeld, Y. et al., (1983)), a monoclonal anti-16/6Id antibody (Mendlovic, S. et al. (1989) *Eur. J. Immun.*, 19:729–734) and T cell lines specific for the 16/6 idiotype (Fricke, H. et al., (1991) *Immunology*, 73:421–427). The strains of mice that may be used include, but are not limited to, Balb, 129, C3H.SW, SJL, AKR, and C3HSW. A preferred method is immunization of mice with a human anti-DNA monoclonal antibody, the 16/6Id antibody (Shoenfeld, Y. et al (1983)). The immunized animals are then exposed to a drug, preferably a MMI analog, and evaluated for alleviation of symptoms of the disease. Parameters evaluated in 16/6Id-treated mice include, but are not limited to, leukopenia, proteinuria, levels of cell surface markers on the peripheral blood lymphocytes (PBL), and immune complex deposits in kidney. Examples of methods for evaluating these parameters include, but are not limited to, analyses of blood cells and sera, tissue biopsies or extracts, urine analyses and analysis of antibody production and immune activated cells. It will be understood by those skilled in the art that conventional methods can be used to evaluate these parameters. Examples of conventional methods that can be used evaluate these parameters include, but are not limited to, cell counts, ELISAs (Heineman, W. R. et al (1987), *Methods of Biochemical Analyses* 32:345–393), quantitative protein assays (Ausubel, J. et al., (1987) in "Current Protocols in Molecular Biology", John Wiley and Sons, New York), immunohistology ("Basic and Clinical Immunology" (1991) Stites, A. P. and Terr, A. I. (eds.) Appelton and Lange, Norwalk, Conn. San Mateo, Calif.), and analysis of cell surface markers on lymphocytes ("Basic and Clinical Immunology" (1991) Stites, D. P. and Terr, A. I. (eds), Appelton and Lange, Norwalk, Conn./San Mateo, Calif.).

In another embodiment of this invention, another in vivo assay is used to assess and develop drugs capable of suppressing expression of MHC Class I molecules. In this in vivo method a tissue to be transplanted into an animal is pretreated with a MHC Class I suppressing drug. Examples of tissues which can be transplanted include, but are not limited to, thyrocytes, hepatocytes, neural tissue, muscle, fibroblasts, adipocytes, and islet cells, endocrine cells and tissues, thyroid, liver, skin, bone marrow, kidney, lung and heart. In a preferred embodiment rat thyroid FRTL-5 cells are pretreated with a MHC Class I suppressing drug prior to transplantation in a rat or mouse. Examples of the means by which the tissue may be transplanted include, but is not limited to, general surgical procedures, intravenous and subcutaneous injection. In a preferred embodiment rat thyroid FRTL-5 cells are subcutaneously injected into the lower back of a rat or mouse. The pretreated transplanted tissue remains in the recipient animal for periods between 30–100 days. Preferably the state of the transplanted tissue is evaluated 60 days after transplantation. One skilled in the art will understand the conventional methods available to evaluate the transplanted tissue. In a preferred embodiment the site of injection of the pretreated transplanted FRTL-5 cells is excised from the recipient animal. The excised tissue is evaluated microscopically for the presence of FRTL-5 cells. In addition FRTL-5 cells are evaluated for the ability of TSH to cause an increase in cAMP levels and an increase in iodide uptake which are indicative of normal FRTL-5 function. The presence of FRTL-5 cells, that had been treated with the candidate drug prior to transplantation, in the excised tissue and that exhibit the increase in TSH mediated cAMP levels or iodine uptake is predictive of the candidate drug's usefulness for preventing or treating transplantation rejection.

In another embodiment of this invention, in vitro assays are used to assess and develop candidate drugs capable of suppressing expression of MHC Class I molecules. One in vitro assay in the present invention relates to a method for assessing the ability of a candidate drug to suppress expression of MHC Class I molecules by detecting altered binding of a protein or proteins in a mammalian cell extract, from cells treated or not treated with the candidate drug, to a MHC Class I regulatory nucleic acid sequence. Extracts from mammalian cells treated with a candidate drug are combined with MHC Class I nucleic acid regulatory sequences and the existence of complexes between said sequences and proteins or protein from the extract is detected. Alterations in binding of mammalian cell protein or proteins to said nucleic acid sequences can be assessed by comparison to binding of protein or proteins to the same MHC Class I regulatory nucleic acid sequence in extracts from untreated cells. By regulatory nucleic acid sequences we mean sequences that regulate transcription of a MHC Class I gene. By alteration we mean an enhancement in the signal of the detected complex in treated versus untreated extracts or a decrease or absence of signal of the detected complex in treated versus untreated extracts. Protein extracts may be either nuclear or cellular extracts; cellular extracts are preferable. Cellular or nuclear protein extracts from mammalian cells are generated by conventional methods (Ausebel, J. et al. (1987) in "Current Protocols in Molecular Biology", John Wiley and Sons, New York).

Examples of nucleic acid sequences that can be used in this in vitro assay include, but is not limited to, DNA fragments containing regulatory sequences of MHC Class I promoters and double stranded oligonucleotides.

Examples of mammalian cells that can be used in this in vitro assay include, but are not limited to, mammalian cell thyrocytes, hepatocytes, neural tissue, muscle, fibroblasts, adipocytes, and HELA cells. Rat FRTL-5 thyroid cells are preferable (American Type Culture Collection, Rockville, MD, ATCC-CRL 8305).

In a one embodiment, the nucleic acid sequences used in this assay are derived from sequences homologous to the DNA regulatory sequences of the MHC Class I gene, PD1. In a preferred embodiment, these nucleic acid sequences are DNA fragments 114, 140 and 238, as shown in FIGS. 9A–9B. The double-stranded oligonucleotides shown in FIG. 10 and designated S1–S8 may also be used or the double-stranded oligonucleotide(K). The K oligonucleotide is the TTF-2 reactive element or regulatory nucleic acid sequence which is in the thyroglobulin promoter (Santisteban, P. et al (1992) *Mol. Endocrinol.*:6:1310–1317) and which is related in sequence to the TTF-2 like site in the silencer complex (FIG. 10).

In a preferred embodiment the ability of a drug to suppress expression of MHC Class I molecules is measured by decreased binding of a protein or proteins in the extract to the above described PD1 DNA fragments or double standard oligonucleotides. By decreased binding we mean a diminution or loss of signal of the detected complexes in treated versus untreated extracts. By complex we mean protein or proteins bound to the nucleic acid sequence.

Detection of the complexes can be carried out by a variety of techniques to one skilled in the art. Detection of the complexes by signal amplification can be achieved by several conventional labelling techniques including radiolabels and enzymes (Sambrook, T. et al (1989) in "Molecular Cloning, A Laboratory Manual," Cold Spring Harbor Press, Plainview, N.Y.). Radiolabelling kits are also commercially available. Preferred methods of labelling the DNA sequences are with $^{32}P$ using Klenow enzyme or polynucleotide kinase. In addition, there are known non-radioactive techniques for signal amplification including methods for attaching chemical moieties to pyrimidine and purine rings (Dale, R. N. K. et al. (1973) *Proc. Natl. Acad. Sci.,* 70:2238–2242; Heck, R. F. (1968) *S. Am. Chem. Soc.,* 90:5518–5523), methods which allow detection by chemiluminescence (Barton, S. K. et al. (1992) *J. Am. Chem. Soc.,* 114:8736–8740) and methods utilizing biotinylated nucleic acid probes (Johnson, T. K. et al. (1983) *Anal. Biochem.,* 133:126–131; Erickson, P. F. et al. (1982) *J. of Immunology Methods,* 51:241–249; Matthaei, F. S. et al. (1986) *Anal. Biochem.,* 157:123–128) and methods which allow detection by fluorescence using commercially available products. Non-radioactive labelling kits are also commercially available. Methods useful to detect complexes of protein extract bound to DNA fragments or double-stranded oligonucleotides include mobility-shift analysis, Southwestern, and immunoprecipitation (Sambrook, J. et al., (1989); Ausubel, J. et al., (1987) in "Current Protocols in Molecular Biology", John Wiley and Sons, New York). A preferred method is gel mobility-shift analysis using a radiolabelled double-stranded nucleic acid sequence. For mobility shift analysis, the protein extract-oligomer complexes can also be detected by using labelled protein extract, wherein the cells can be metabolically labelled with $^{35}S$, or tritiated thymidine. Alternatively, radioiodination with $^{125}I$ or non-radioactive labelling using biotin and various fluorescent labels prior to the preparation of the protein extract may also be used.

A second in vitro assay of the invention relates to a method for assessing the ability of a drug to suppress expression of MHC Class I by measuring the activity of a reporter gene operably linked downstream of a MHC Class I promoter and its regulatory sequences. The reporter gene operably linked to a MHC Class I promoter and its regulatory sequence is introduced into mammalian cells, said mammalian cells are treated with the candidate drug and the activity of the reporter gene in lysates from treated and untreated mammalian cells is measured. A decrease of activity of the reporter gene in cell lysates from treated versus nontreated cells is predictive of the usefulness of the candidate drug in suppressing MHC Class I expression.

Preferred regulatory sequences that may be operably linked to the reporter gene are sequences corresponding to the silencer/enhancer region of the MHC Class I, PD1 gene. These sequences are 114, 140, 151 and 238, as shown in FIGS. 9A–9B, with their cognate promoters. It will be understood by one skilled in the art that sequentially and functionally homologous regions found in the regulatory and promoter domains of other Class I genes may also be used. Examples of reporter genes include, but are not limited to, the chloramphenicol acetyltransferase (CAT) gene, the β-galactosidase gene, the luciferase gene and human growth hormone (hGH) (Sambrook, J. et al. (1989); Ausubel, F. et al. (1987) in "Current Protocols in Molecular Biology" Supplement 14, section 9.6 (1990); John Wiley and Sons, New York). Examples of mammalian cells that can be used in this in vitro assay include, but are not limited to, mammalian cell thyrocytes, hepatocytes, neural tissue, muscle, fibroblasts, adipocytes, and HELA cells. The means by which the regulatory sequence operably linked to the reporter gene may be introduced into cells are the same as those described above. In a preferred embodiment the CAT gene is operably linked to one of the above mentioned PDI sequences and introduced into FRTL-5 cells.

It is understood by one skilled in the art that the ability of a candidate drug to suppress expression of MHC Class I molecules can also be assessed by comparing levels of cellular mRNA in mammalians cells treated with the candidate drug versus cells not treated with the candidate drug. Examples of methods for determining cellular mRNA levels include, but is not limited to Northern blotting (Alwine, J. C. et al. (1977) *Proc. Natl. Acad. Sci.,* 74:5350–5354), dot and slot hybridization (Kafatos, F. C. et al. (1979) *Nucleic Acids Res.,* 7:1541–1522), filter hybridization (Hollander, M. C. et al. (1990) *Biotechniques;* 9:174–179), RNase protection (Sambrook, J. et al. (1989) in "Molecular Cloning, A Laboratory Manual", Cold Spring Harbor Press, Plainview, N.Y.), polymerase chain reaction (Watson, J. D. et al.) (1992) in "Recombinant DNA" Second Edition, W. H. Freeman and Company, New York) and nuclear run-off assays (Ausubel, F. et al. (1989) in "Current Protocols in Molecular Biology" Supplement 9 (1990); John Wiley and Sons, New York).

The MHC Class I suppressing drugs which are administered according to this invention may be administered as a sterile pharmaceutical composition further comprising a biologically acceptable carrier including, but not limited to, saline, buffer, dextrose, ethanol and water.

The MHC Class I suppressing drugs which are administered may be administered alone or in combination with other drugs, hormones, or antibodies. Examples of drugs include, but are not limited to, MHC Class I suppressing drugs, immunosuppressive drugs, cytotoxic drugs and anti-inflammatory drugs. Examples of hormones include, but are not limited to, corticosteroids, steroids and steroid derivatives, estrogens, androgens, growth factors such as insulin-like growth Factor I, glycoprotein hormones, cytokines and lymphokines. Examples of antibodies include, but are not limited to, antibodies directed against MHC Class I antigens, antibodies directed against MHC Class II antigens and antibodies against infectious antigens.

Means of administering the MHC Class I suppressing drugs include, but are not limited to, oral, sublingual, intravenous, intraperitoneal, percutaneous, intranasal, intrathecal, subcutaneous, intracutaneous, or enteral. Local administration to the afflicted site may be accomplished through means known in the art, including, but not limited to, topical application, injection, infusion and implantation of a porous device in which the MHC Class I suppressing drugs are contained.

A preferred means of administering the MHC Class I suppressing drugs in the treatment of autoimmune diseases and transplantation rejection is oral. A preferred means of pretreating tissues to be transplanted is by perfusion in vitro with an aqueous solution.

All books, articles, or patents referenced herein are incorporated by reference. The following examples illustrate various aspects of the invention but are no way intended to limit the scope thereof.

EXAMPLE 1

Lack of Induction of Experimental SLE in MHC-Class I-Deficient Mice

Induction of Experimental SLE in Mice

Systemic lupus erythematosus (SLE) is an autoimmune disease characterized by the presence of an array of autoantibodies, among these are anti-DNA, anti-nuclear antigen, and anti-RNP antibodies (Talal, N. et al. (1977) Autoimmunity: Genetic, Immunology Virology and Clinical Aspects; Academic Press, New York ). Progression of the disease in humans is correlated with leukopenia, proteinuria, and immune complex deposits in the kidney and other organs. An experimental model of SLE can be induced in mice by immunization with a human monoclonal anti-DNA antibody expressing a common idiotype, designated 16/6Id. Following a single immunization and subsequent boost with the 16/6Id, mice produce antibodies to the 16/6Id, to DNA, and to nuclear antigens. After a period of 4–6 months, the immunized mice develop leukopenia and proteinuria, and immune complexes are observed in their kidneys (Mendlovic, S. et al, (1988) *Proc. Natl. Acad. Sci. U.S.A.*, 85:2260–2264). This experimental model closely parallels the human disease with respect to the production of autoantibodies and to its clinical manifestations. Several other laboratories have used these antibodies to induce SLE in mice. The immunological basis for disease induction in 16/6Id-immunized mice is not known. Mice lacking cell-surface MHC class I molecules have been generated by inactivating the gene for $\beta_2$ microglobulin, which is required for the proper assembly and cell surface expression of the class I molecule (Zijlstra, M. et al., (1990) *Nature*, 344:742–746; Koller, B. et al., (1990) *Science*, 248:1227–1230; mice were provided by B. Koller). These Class I-deficient mice also fail to develop the $CD4^- CD8^+$ T cell subset. Class I-deficient mice generally are healthy and capable of generating antibody responses and surviving various viral infections; however, they are more sensitive to intracellular parasites than their normal littermates. To determine whether class I molecules play any role in the induction or propagation of experimental SLE, class I-deficient mice were tested for their ability to develop this disease.

Mice (groups of 4–6; strain 129-class I deficient) were immunized intradermally into the hind footpads with 1 ug of affinity purified human monoclonal 16/6Id in complete Freund's adjuvant (CFA; Difco, Detroit, Mich. ) and boosted 3 weeks later with 1 ug of 16/6Id in phosphate-buffered saline (PBS) (Mendlovic, S. et al, (1988) *Proc. Natl. Acad. Sci. U.S.A.*, 85:2260–2264). Immunization of strain 129-Class I-deficient mice with chicken ovalbumin (Grade v. sigma Chem. Co. St. Louis, Mo. ) was at 2 ug and followed the same regimen as 16/6Id.

Analysis of Anti-16/61d and Anti-DNA Antibodies In Class I-Deficient Animals

Figure 1A:
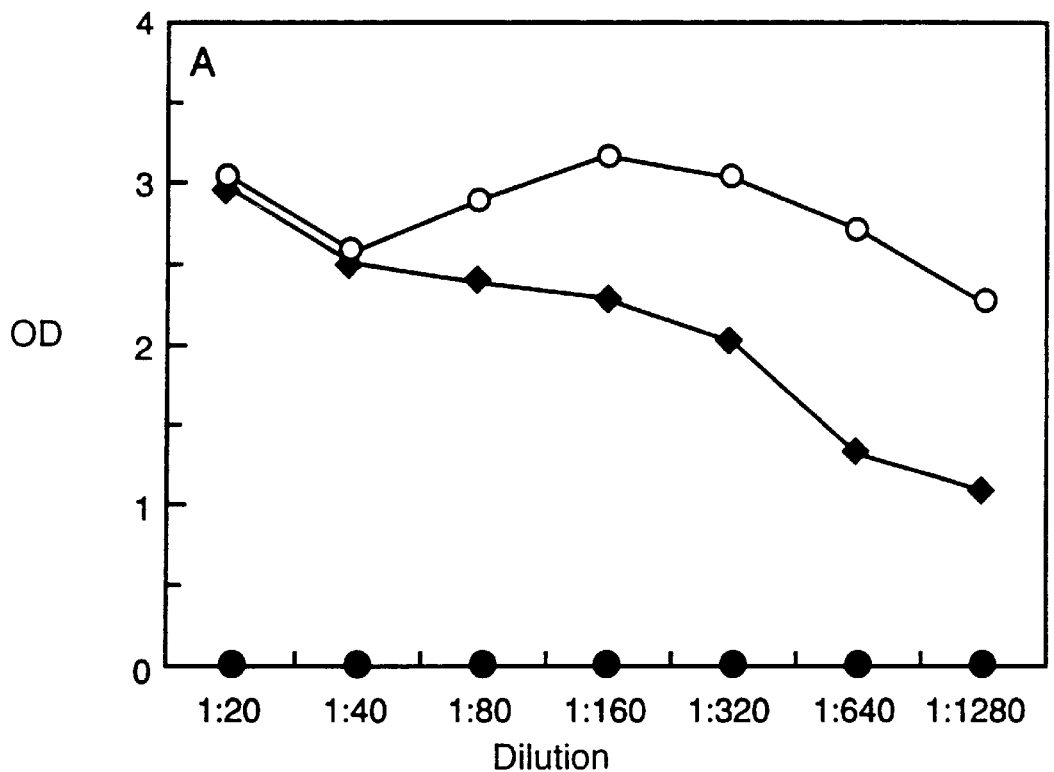
FIGS. 1A–1D shows that Class I-deficient mice generate anti-16/6Id antibodies, but not anti-DNA or anti-nuclear antigen antibodies. Serial two-fold dilutions of sera were assayed by ELISA 10 weeks after immunization. Results are the average of measurements of 5 individual animals and are expressed as OD at 405 nm×10$^3$, as a function of serial serum dilutions. Standard deviation values did not exceed 10% of the mean. Sera of 16/6Id-immunized control 129 mice (○), 16/6Id-immunized Class I-deficient mice (♦), and ovalbumin-immunized Class I-deficient mice(●).
Figure 1B:
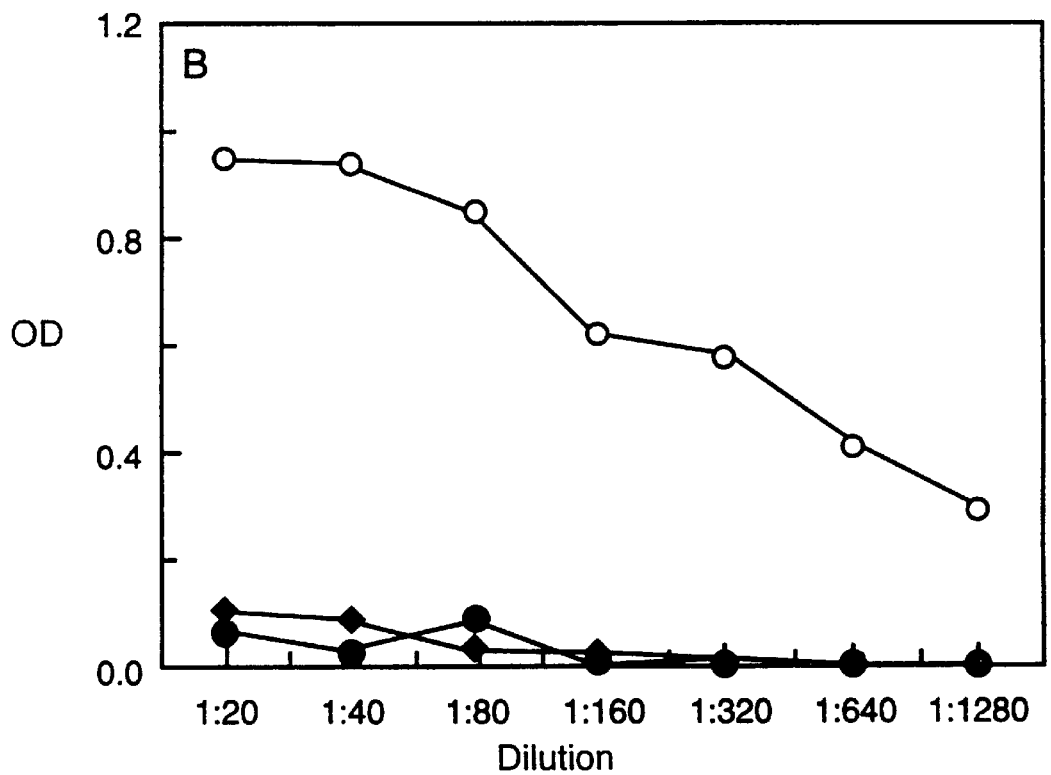
Figure 1C:
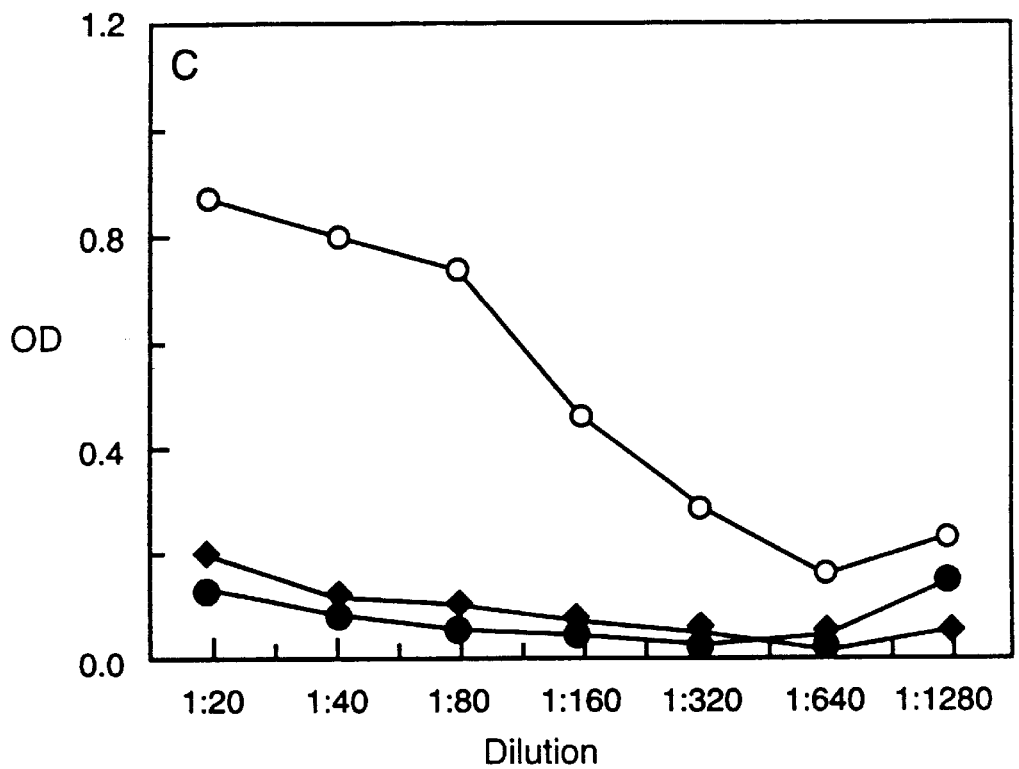
Figure 1D:
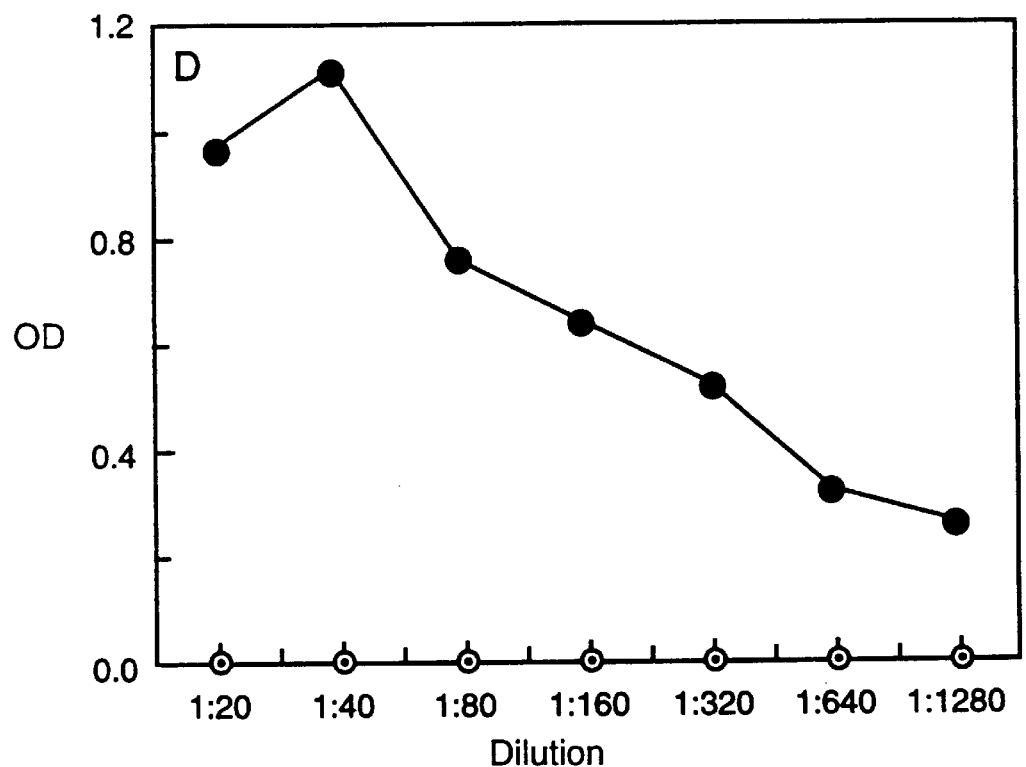
Figure 2A:
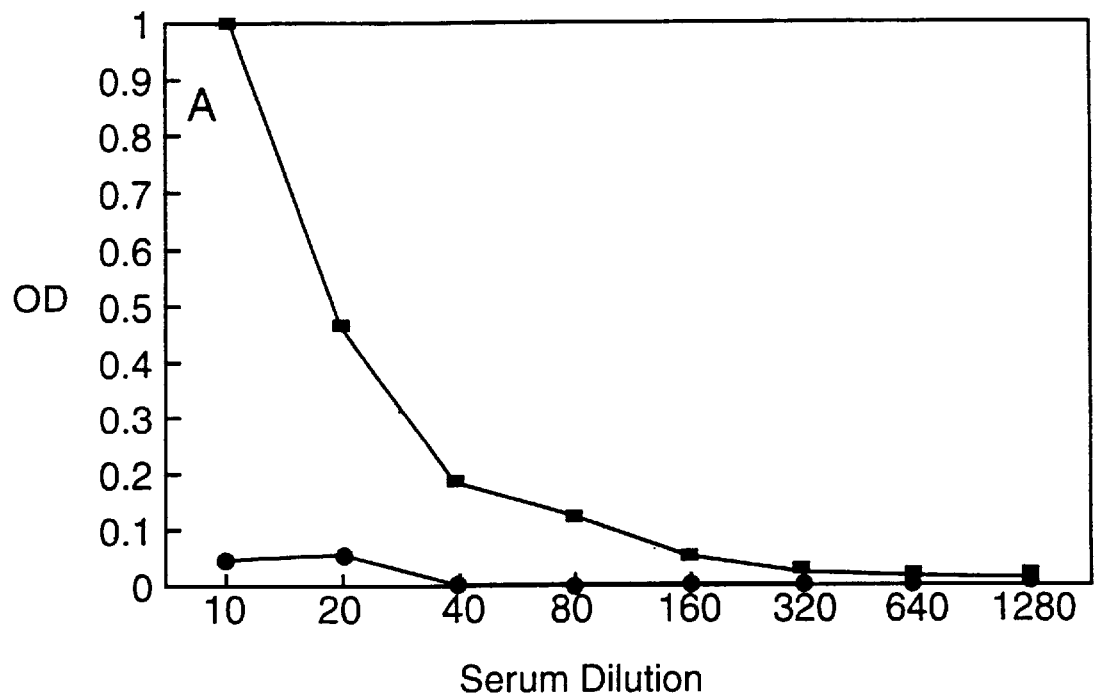
Figure 2B:
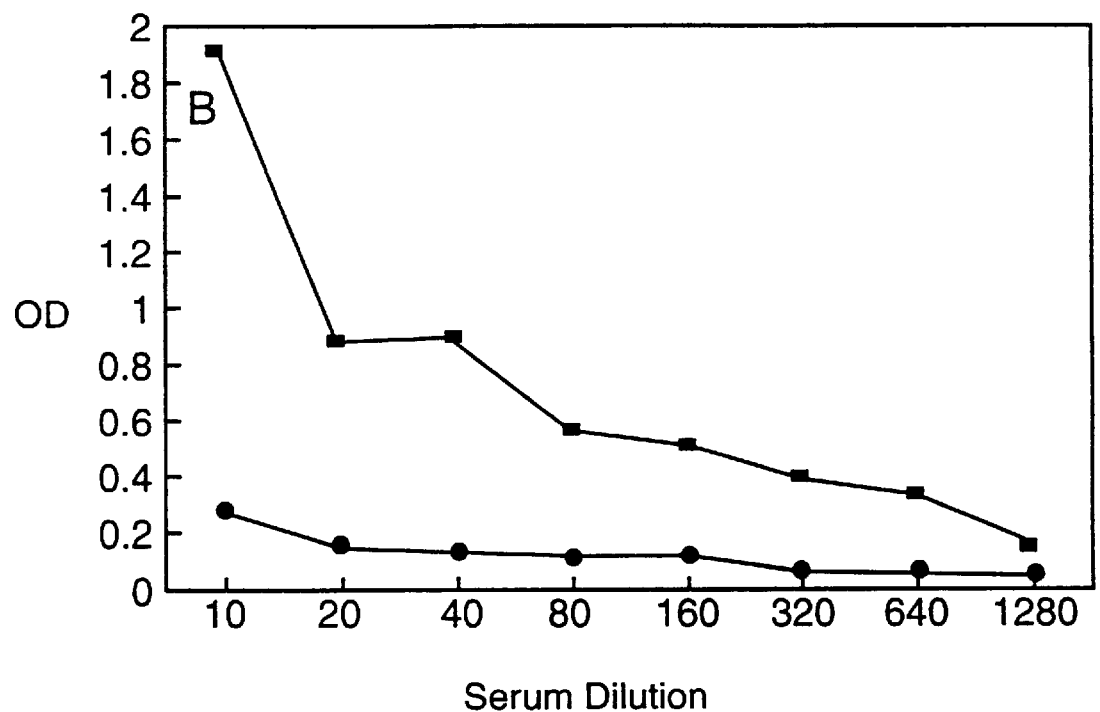
Figure 2C:
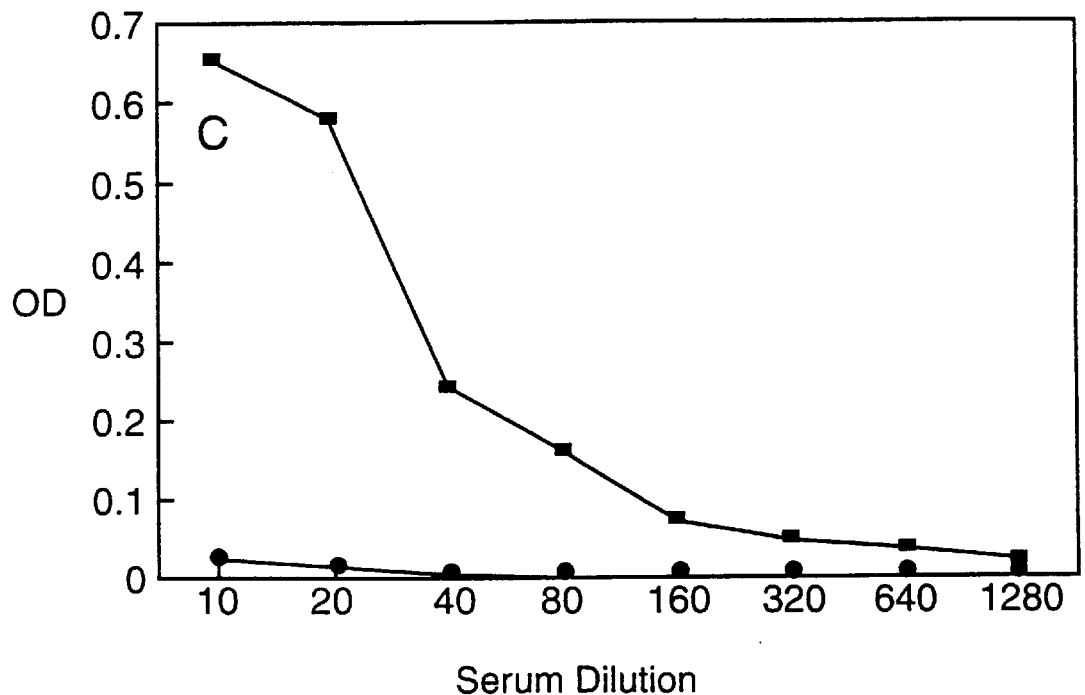
Figure 2D:
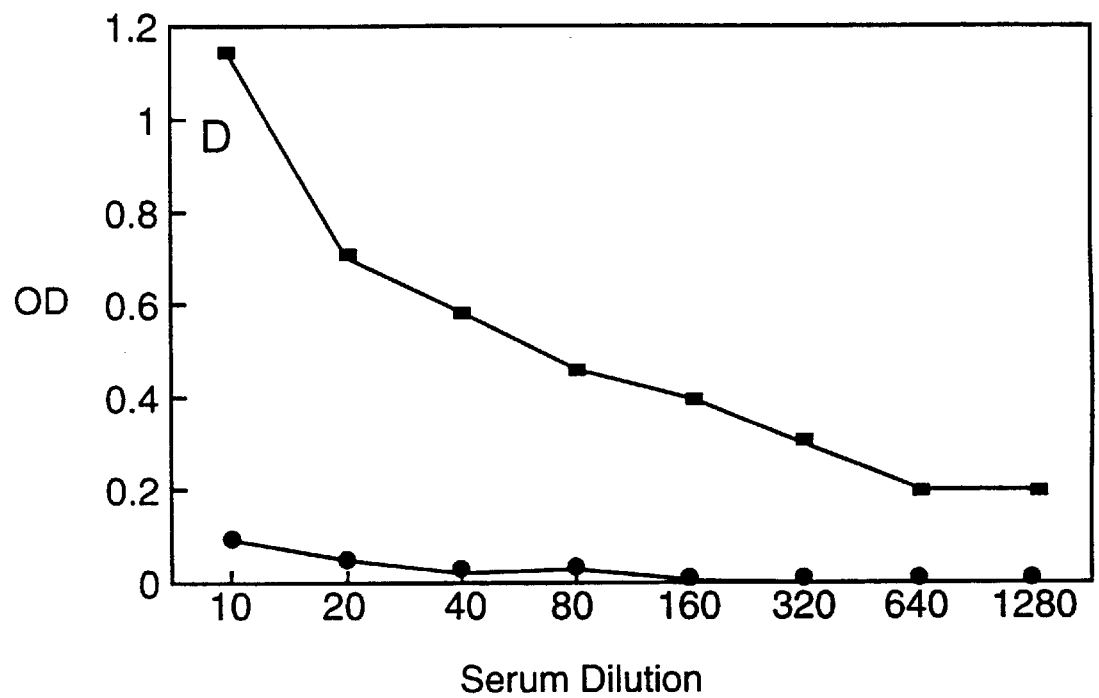

In Class $I^+$ control strain 129 mice (Jackson Labs, Bar Harbor, Me.), anti-16/6Id and anti-DNA responses were detected in the sera by ELISA. ELISAs were performed using 16/6Id and anti-16/6Id as described (Mendlovic, S. et al., (1988), *Proc. Natl. Acad. Sci.* (USA) 85:2260–2264; Heineman, W. R. et al (1987) *Methods Of Biochemical Analysis* 32:345–393). Anti-16/6Id and anti-DNA responses were detected within 10 days post-boost and persisted for at least 6 months; results are shown from animals 10 weeks after the boost (FIG. 1A and 1B). Sera from 16/6Id-immunized animals did not contain significant anti-human immunoglobulin reactivity. Class I-deficient mice immunized with the 16/6Id developed anti-16/6Id antibodies at the same time as, and with titers not significantly different from, the control strain 129 mice (FIG. 1A). In contrast, sera of the Class I-deficient mice did not contain significant anti-DNA antibody (FIG. 1B); no significant anti-DNA response was detected in the class I-deficient animals for up to at least 6 months. During this time, anti-16/6Id titers remained high in the sera of both class I-deficient and control strain 129 animals. Furthermore, anti-nuclear antigen antibodies were not detected in sera of class I-deficient animals, but were found in sera of 16/6Id-immunized strain 129 animals. (FIG. 1C). The class I-deficient mice were not generally poor responders to antigen, as immunization with ovalbumin elicited an antibody response not markedly different from that of normal mice (FIG. 1D).

It has previously been reported that C57BL/6 mice are non-responders to the 16/6Id (Mendlovic, S. et al., (1990) *Immunology*, 69:228–236). Since the C57BL/6 mice failed to generate anti-16/6Id antibodies, this non-response is distinct from that of the class I-deficient mice which made anti-16/6Id antibodies, but no anti-DNA or anti-nuclear antigen antibodies. Furthermore, C57BL/6 X Class I-deficient F1 mice responded normally to the 16/6Id.

Response of Class I-Deficient Animals to Immunization With Monoclonal Anti- 16/6Id Antibody The development of anti-DNA antibodies in normal mice immunized with 16/6Id is correlated with the generation of anti-anti-16/6Id antibodies (Mendlovic, S. et al., (1988) *Proc. Natl. Acad. Sci. U.S.A.* 85:718–730); immunization with anti-16/6Id triggers antibodies to DNA and nuclear extract, and experimental SLE (Mendlovic, S., et al., (1989) *Eur. J. Immunol*, 19:2260–2264). The failure of Class I-deficient mice to develop anti-DNA antibodies in response to immunization with 16/6Id raised the possibility that they do not respond to anti-16/6Id. This possibility was assessed by immunizing class I-deficient mice with murine monoclonal anti-16/6Id.

Mice (groups of 6) were immunized in the hind foot pads with 20 $\mu$g of monoclonal, anti-16/6Id 1A3–2 (Mendlovic, S. et al., (1989) *Eur. J. Immunol*, 19:729–734) in CFA and boosted 3 weeks later with the same amount of monoclonal antibody in PBS. Mice injected with a control anti-Id antibody (Mendlovic, S. et al. (1989) *Eur. J. Immunol* 19:729–734) did not develop a response. Although the control strain 129 mice all responded to the anti-16/6 idiotype, the class I-deficient mice did not respond at all (FIG. 2). Thus, class I-deficient mice are capable of responding to ovalbumin and 16/6Id, but they are defective in their response to anti-16/6Id antibody (FIG. 1 and 2).

Analysis of Leukopenia, Proteinuria and Immune Complex Disease in Normal and Class I-Deficient Mice Immunized with 16/6Id Immunization of control 129 mice with 16/6Id not only elicited an extended antibody response, but also induces leukopenia, proteinuria, and immune complex disease in the kidney (Table 1, FIG. 3). Since Class I-deficient mice did not mount the full range of antibody responses following 16/6Id immunization, their susceptibility to these clinical manifestations of disease was monitored. Whole blood was collected from the tail vein of the mice into heparin diluted 1:10 in PBS, followed by a 1:10 dilution in 1% acetic acid in distilled water to lyse the red blood cells. Leukocytes were then microscopically counted in a hemocytometer using conventional methods. Protein levels in urine were measured by conventional colormetric assays on Ames 2855 Uristix (Miles, Inc.). None of the Class I-deficient mice showed any evidence of either leukopenia or proteinuria (Table I). Assessment of immune complex disease in the kidney of control and Class I-deficient animals was determined by immunohistology using frozen kidney sections, 5 μm thick, fixed and stained with FITC-conjugated goat antimouse IgG as previously described (gamma chain specific: Sigma Immunochemicals St. Louis, Mo.; Fricke H. et al. (1991) *Immunology*, 73:42–427). Immune complex deposits were readily detected in the kidneys of 16/6Id-immunized control mice; no such deposits were found in the kidneys of class I-deficient animals (FIG. 3). Taken together, these data indicate that class I-deficient mice do not develop experimental SLE.

TABLE 1

Class I-Deficient Mice Immunized With 16/6Id
Do Not Develop Clinical Manifestations of SLE

| Animals | Treatment | Leukocyte Counts (#/mm³) | Proteinuria (mg/dL) |
|---|---|---|---|
| Experiment #1: | | | |
| 129 | None | 5500 ± 250 | Negative |
| 129 | 16/6Id | 3150 ± 50 | 100 |
| Class I-deficient | None | 5500 ± 250 | Negative |
| Class I-deficient | 16/6Id | 5530 ± 250 | Trace |
| Class I-deficient | Ovalbumin | 5130 ± 155 | Negative |
| Experiment #2: | | | |
| 129 | None | 5500 ± 3000 | Negative |
| 129 | 16/6Id | 2680 ± 135 | 30–100 |
| Class I-deficient | None | 5500 ± 250 | Negative |
| Class I-deficient | 16/6Id | 4480 ± 193 | Negative-Trace |
| Class I-deficient | Ovalbumin | 4033 ± 88 | Negative |

Legend to Table 1. Five or six months after immunization, blood was drawn from class I-deficient and control 129 mice. Leukocyte counts were performed on each individual animal. The results represent the mean±SEM. The leukocyte counts of the 16/6Id immunized class I-deficient and control 129 animals are significantly different (p<0.002); those of the class I-deficient mice immunized with 16/6Id or ovalbumin are not significantly different (p<0.2), and fall within the normal range. Protein in the urine was measured using an Ames 2855 Uristix (Miles, Inc.); normal mice were negative.

EXAMPLE 2

MMI as a Therapeutic Drug in SLE Mice

As described in Example 1, to induce experimental SLE, Balb/c mice were immunized intradermally with human monoclonal anti-DNA antibody, 16/6Id, in complete Freund's adjuvant and boosted 3 weeks later with 16/6 Id in saline. Anti-16/6Id antibodies could be detected in all mice within two weeks of the boost (FIG. 4). After two weeks, mice were treated with a subcutaneous injection of MMI in pellet form, which results in a 30 day release of the drug. The pellet in these experiments contained 15 mg MMI (0.5 mg released per day; Innovative Research of America, Toledo, Ohio). Treatment was repeated 30 days later. Several groups of 16/6Id immunized mice were evaluated: mice treated with MMI alone, with MMI plus thyroxine (1.5 mg/pellet, 30 day release, Innovative Research of America, Toledo, Ohio) to prevent hypothyroidism, or with a MMI placebo (Innovative Research of America, Toledo, Ohio). In addition, normal mice that had not been immunized with 16/6Id were treated with an identical drug regimen. Mice were bled at regular intervals and monitored by various parameters. Serum was assayed for the presence of anti-16/61d antibodies and anti-DNA antibodies by ELISA, as described in Example 1. Peripheral blood cells were counted and analyzed for expression of various cell surface markers, including MHC class I and class II, by flow cytometry using labelled specific antibodies which are commercially available. In addition, protein in the urine was measured as described in Example 1. Finally, after 6 months, mice were sacrificed and kidneys analyzed for immune complex deposits. Immunohistology was performed as described in Example 1.

Effect of MMI on the formation of anti-16/61d and anti-DNA Antibodies

Within two weeks of the 16/6Id boost, both anti-16/6Id and anti-DNA antibodies were detected in all of the immunized mice (FIG. 4). In untreated, control mice, the anti-16/6Id antibody titers increased for 4–8 weeks post boost and the anti-DNA antibody titers increased for four weeks post boost; both persisted for the duration of the experiment. MMI treatment of 16/6Id immunized mice resulted in a small but reproducible decrease in the level of anti-16/6Id antibody titer over the 4 month post treatment period (Table II-A, FIG. 4). Anti-DNA antibody titers were markedly lower in MMI-treated than untreated 16/6Id immunized animals (Table II-B; FIG. 4). Treatment with thyroxine ($T_4$), together with MMI, partially reversed the decrease in anti-16/6Id antibody titers (Table II; FIG. 4) but did not significantly affect anti-DNA antibody titers (Table 2; FIG. 4). Placebo alone caused a modest inhibition in antibody titers, but never as much as that of MMI. Taken together, these data demonstrate that MMI treatment caused a decreased generation of anti-DNA antibodies.

TABLE II

| Rx[a] | 0 weeks | 3 weeks | 4 weeks | 7 weeks | 9 weeks | 12 weeks | 22 weeks |
|---|---|---|---|---|---|---|---|
| A. Relative Anti-16/6Id Antibody Titers | | | | | | | |
| 16/6Id | 1.0 | 1.0 | 1.0 | 1.0 | 1.0 | 1.0 | 1.0 |
| 16/6Id + MMI | 0.77 | 0.71 | 0.74 | 0.86 | 0.68 | 0.65 | 0.54 |
| 16/6Id + MMI + $T_4$ | 0.82 | 0.71 | 0.97 | 0.93 | 1.0 | 0.97 | 0.83 |
| 16/6Id + placebo | — | — | 0.89 | 0.94 | 0.83 | — | — |
| MMI | 0.0 | 0.0 | 0.0 | — | 0.0 | 0.05 | 0.0 |

TABLE II-continued

| Rx[a] | 0 weeks | 3 weeks | 4 weeks | 7 weeks | 9 weeks | 12 weeks | 22 weeks |
|---|---|---|---|---|---|---|---|
| MMI + $T_4$ | 0.0 | 0.0 | 0.0 | — | 0.0 | 0.05 | 0.0 |
| Placebo | — | — | 0.01 | — | 0.0 | — | — |
| B. Relative Anti-DNA Antibody Titers | | | | | | | |
| 16/6Id | 1.0 | 1.0 | 1.0 | 1.0 | 1.0 | 1.0 | 1.0 |
| 16/6Id + MMI | 2.18 | 0.67 | 0.16 | 0.11 | 0.17 | 0.18 | 0.0 |
| 16/6Id + MMI + $T_4$ | 2.18 | 0.67 | 0.16 | 0.11 | 0.17 | 0.18 | 0.0 |
| 16/6Id + placebo | — | — | 0.53 | 0.49 | 0.46 | — | — |
| MMI | 0.14 | 0.08 | 0.03 | 0 | 0.03 | 0.16 | 0.0 |
| MMI + $T_4$ | 0.14 | 0.18 | 0.038 | — | 0.19 | 0.0 | — |
| Placebo | — | — | 0.08 | — | 0.15 | — | — |

[a]The column designated Rx indicates treatment received by animals.

Effect of MMI on the development of leukopenia and proteinuria

A characteristic feature of this SLE model, is that mice treated with the 16/6Id antibody develop leukopenia as a function of time and as one of the clinical manifestations of the developing disease. (FIG. 5). Mice immunized with 16/6Id and treated with MMI did not develop leukopenia (FIG. 5). The effect of MMI was not prevented by simultaneous treatment with thyroxine (FIG. 5) nor was it duplicated by placebo treatment. The protective effect of MMI persisted at least 4 months after MMI treatment was discontinued. Furthermore, proteinuria, which is a clinical manifestation in 16/6Id immunized mice, was prevented by MMI treatment.

Effect of MMI on the development of immune complexes in the kidney

After 4–6 months, mice immunized with 16/6Id developed immune complex deposits in the kidney which are associated with death due to renal failure (FIG. 6, left). Kidneys were isolated from mice five months after MMI treatment ended, frozen and stained as described in Example 1. The pattern of immune complexes observed in the kidneys of 16/6Id immunized animals was similar to that in human kidneys derived from SLE patients (FIG. 6A). MMI treatment of 16/6Id immunized mice markedly reduced the development of kidney lesions (FIG. 6B. The effect of MMI is not prevented by simultaneous treatment with thyroxine nor was it duplicated by placebo treatment. The effect is evident for at least five months after MMI treatment.

Effect of MMI on lymphocyte populations during the course of the experimental disease Although MMI has been used extensively in the treatment of autoimmune thyroid disease, its effect on various lymphocyte populations and cell surface expression of MHC antigens has not been assessed previously. Since MMI has been shown to repress MHC class I transcription in vitro (Saji et al., 1992b) and because of its ability to mitigate the onset of experimental SLE, its effect on lymphocytes in vivo was evaluated.

Figure 7A:
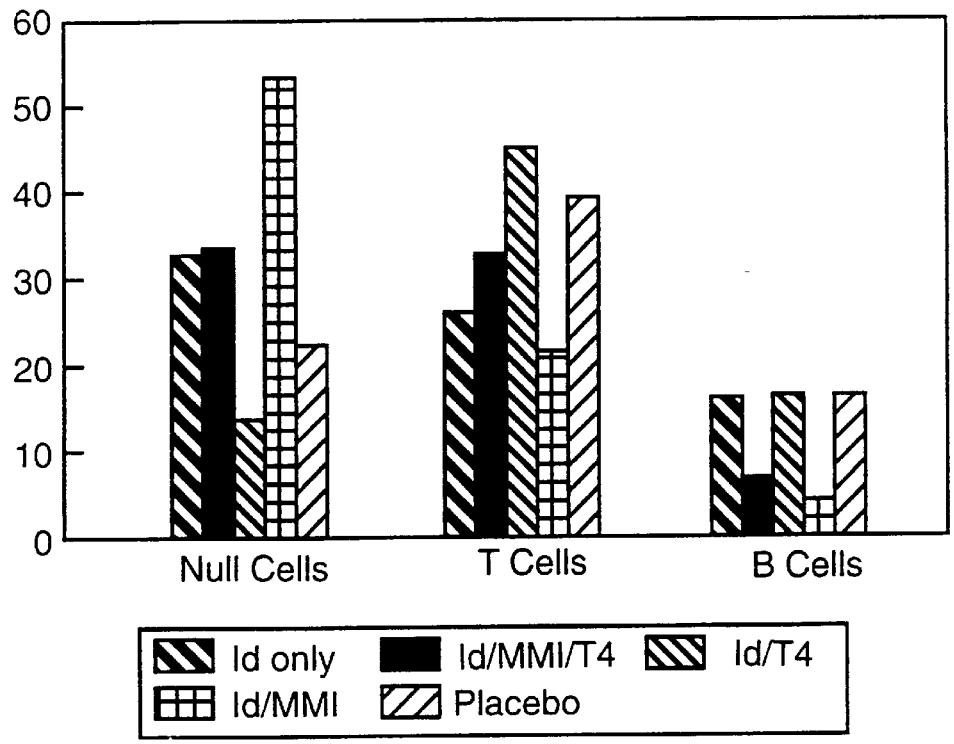

According to the method described in Ehrlich, R. et al. (1989) Immunogenetics 30:18–26, peripheral blood lymphocytes (PBL) from 16/6Id-immunized mice, either MMI treated or not, were analyzed by flow cytometry for the proportion of T cells and B cells after MMI treatment. T cells were identified by their expression of the cell surface marker, Thy1, and B cells by their expression of B220 or MHC class II as detected by specific antibodies to these markers. Antibodies against these MHC Class I and MHC Class II surface markers, as well as others, are commercially available (Pharmingen, Boehringer—Mannheim; Erlich, R. et al. (1989) Immunogenetics 30:18–26). PBL from 16/6Id immunized mice consistently contained 15–20% B cells and 25–30% T cells (FIG. 7A). The remainder being neither B cells nor T cells and are termed null cells (FIG. 7A). This distribution did not vary markedly over the course of 6 months. Whereas MMI treatment had little or no effect on the proportion of T cells, it markedly reduced the fraction of B cells in the PBL (FIG. 7A). There was a concomitant increase in the fraction of unstained cells. These changes in cell populations were most marked immediately after MMI treatment, but persisted for up to 2 months after MMI treatment had been discontinued. Thyroxine treatment, in conjunction with MMI, tended to partially reverse these effects.

Figure 7B:
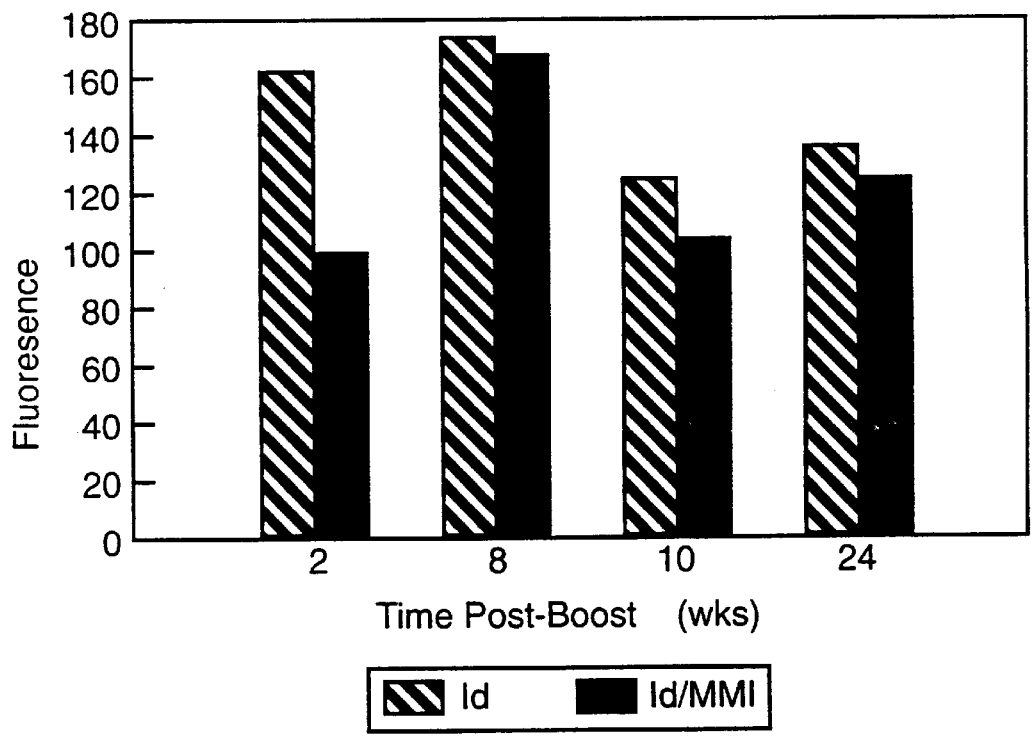
Figure 7C:
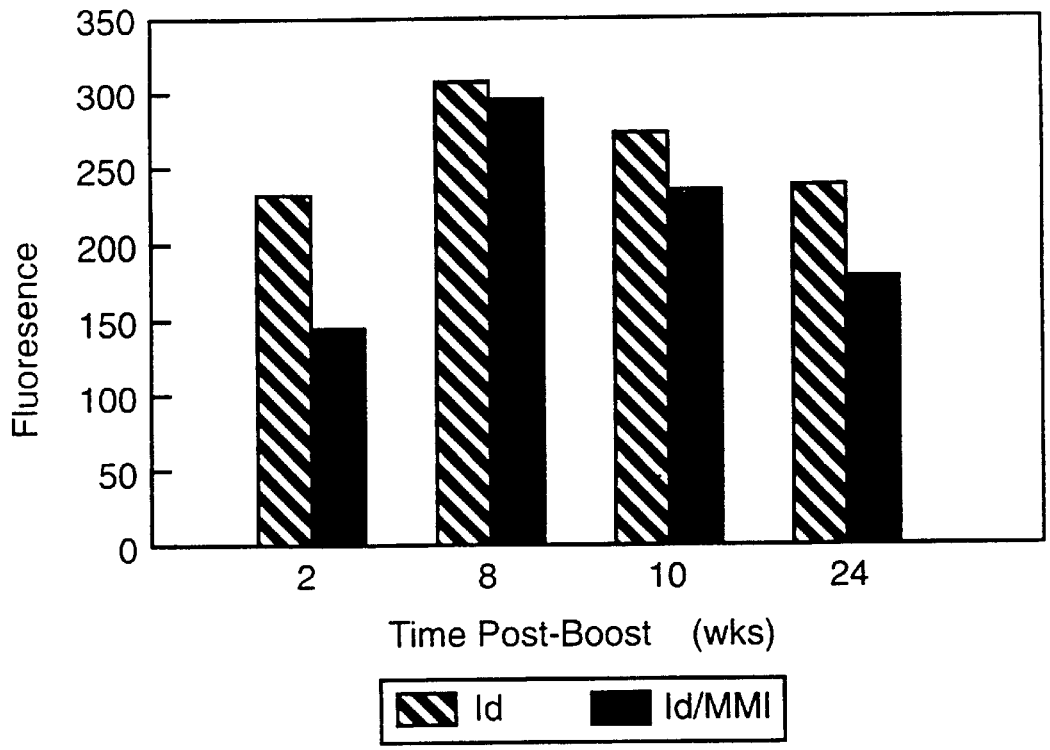
Figure 7D:
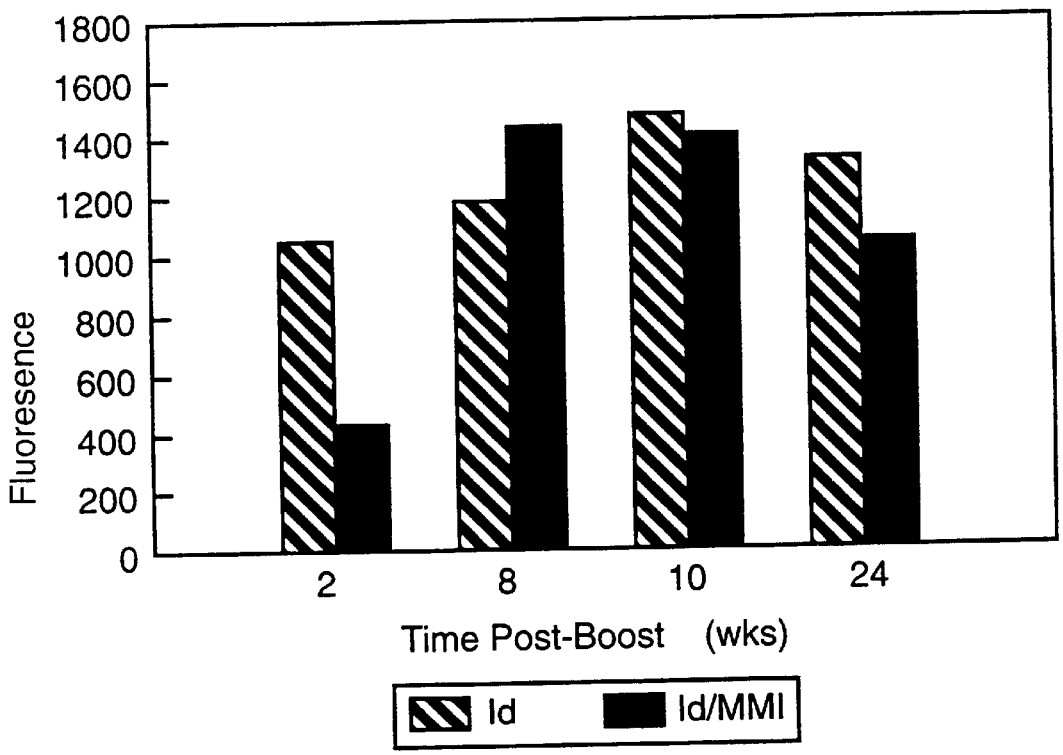

The levels of MHC cell surface expression of the T and B cell populations were assessed by two-color flow cytometry (Ehrlich, R. et al. (1989)). PBL from 16/61d treated animals did not express levels of MHC class I or class II significantly differently from non-immunized controls. MMI treatment resulted in a decrease in MHC class I expression on the surfaces of both T cells and B cells (FIGS. 7B, 7C). In addition, MHC class II levels on B cells were also reduced (FIG. 7D). These effects were most pronounced at early times after the 16/6Id boost and within one week after MMI treatment. As assessed by flow cytometry (Ehrlich, R. et al. (1989)), other cell surface markers were not affected by MMI.

EXAMPLE 3

MMI as a Therapeutic Drug in NZB Mice

NZBxNZWF1 mice (Jackson Labs, Bar Harbor, Me.) spontaneously develop SLE (Steinberg, A. D. et al. (1990) Immunological Reviews 118:129–163; "Cellular and Molecular Immunology" (eds.) Abbas, Lichtman and Ruber (1992), page 360). These mice also spontaneously develop kidney lesions and produce anti-DNA autoantibodies.

NZBxNZWFI mice at six weeks of age, at which time there are no SLE symptoms, were started on MMI therapy. One 30 day MMI pellet (15 mg MMI) was injected subcutaneously every month as described in Example 1. Anti DNA antibodies in the serum were titered by ELISA monthly, as described in Example 1 and Example 2. As shown in FIG. 8, MMI markedly decreased the anti-DNA titer after two months in this spontaneous disease model as in the 16/6Id model (Examples 1 and 2; FIGS. 1, 2 and 4). The effect of MMI on anti-DNA antibodies was even more pronounced three months after treatment.

EXAMPLE 4

MMI as a Treatment for SLE in Humans

For treating humans suffering from SLE MMI is administered orally. Initially in a dose of up to 100 mg per day. This can be followed by a step-wise program, to 50 mg for up to 20 days, 40 mg for up to 20 days, 35 mg for up to 30 to 60 days, decreasing progressively to 5 mg–30 mg per day. A maintenance dose of 5 mg–10 mg per day for up to 1 year or longer can also be used. TSH levels can be monitored to assess the therapeutic levels of MMI required for the SLE patient. When TSH levels increase significantly above the normal range, MMI dosage can be decreased to the next dose level. Alternatively, thyroid hormone levels can be used to determine dosage changes of MMI. A significant decrease from the normal range can be used as an indication to lower dosage. Since patients can be treated with thyroid hormone ($T_4$ or $T_3$) plus MMI to maintain a euthyroid state, the TSH level is a better index. The same parameters may be assessed in children.

Patients can be monitored for alleviation of clinical signs and symptoms of active disease. Specifically monitored parameters can include, autoantibodies, particularly DNA antibodies, PBL cell surface markers, leukopenia, proteinuria, hyperimmunoglobulinemia and levels of immune complexes in the kidney by punch biopsy.

EXAMPLE 5

In Vitro Treatment Of FRTL-5 With Methimazole For Transplantation Into Wistar Rats or Balb/c Mice Rat FRTL-5 (American Type Culture Collection, Rockville, Md.; CRL 8305; U.S. Pat. No. 4,609,622; U.S. Pat. No. 4,608,341) cells were grown to near confluency in complete 6H medium and then exposed, or not, to methimazole, 5 mM, for 72 hours in the presence of the normal complete 6H medium (Saji et al. (1992b) Cells from 4 plates were then harvested by trypsinization as per cell transfer, scraping, or with cold HBSS (Hanks Balanced Saline Solution) plus EDTA, 2 mM. Cells were centrifuged as for splitting cells, resuspended in complete medium, recentrifuged and suspended in 0.1 to 0.2 ml medium. Cells were then injected subcutaneously, in the lower back, into normal Balb/c mice (NIH; Jackson Labs, Bar Harbor, Me.) or Wistar rats (NIH; Jackson Labs, Bar Harbor, Me.). Sixty days later, cells from the site of injection were isolated by surgical excision of the entire implantation site and exposed to a mixture of collagenase trypsin, and chicken serum (CTC; Kohn, L. D. et al. U.S. Pat. No. 4,609,622 Ambesi-Impiombato U.S. Pat. No. 4,608,341; Kohn, L. D. and W. A. Valente, *FRTL-5 Today*, (eds) F. S. Ambesi-Impiombato and H. Perrild (1989):244–273)) to isolate individual cells, then plated in Petri dishes in normal 6H medium. Thyroid cell presence was evaluated microscopically; however, in all cases cells were cultured to confluency, subcultured in 24 well plates in 6H medium, then maintained 5 days without TSH before measuring TSH-induced iodide uptake or TSH-induced cAMP levels (Kohn et al., U.S. Pat. No. 4,604,622). The increase induced by TSH was compared to control cells not treated with TSH. Thyroid cells (FRTL-5) were found only in cultures from the site of injection in which cells were pretreated with MMI (Table III). The cultures containing these thyroid cells also exhibited TSH-increased cAMP levels and TSH increased iodide uptake (Table III). In contrast, cultures from the site of injection in which the FRTL-5 cells had not been pretreated with MMI contained only fibroblast cells (Table III). In addition, no TSH increased cAMP levels or TSH increased iodide update were observed. These results show that pretreatment of FRTL-5 cells with MMI prevents rejection after transplantation. Simultaneously cultured FRTL-5 cells were positive controls. Four animals were in each group. The experiment was repeated with similar results.

TABLE III

| | No MMI | Plus 5 mM MMI |
|---|---|---|
| Balb/c mice | | |
| Microscopy | Fibroblasts only | Thyroid cells plus fibroblasts |
| TSH increased cAMP | No | Yes (8 ± 3 fold) |
| TSH increased iodide uptake | No | Yes (5 ± 1.5 fold) |
| Wistar rats | | |
| Microscopy | Fibroblasts only | Thyroid cells plus fibroblasts |
| TSH increased cAMP | No | Yes (10 ± 3 fold) |
| TSH increased iodide uptake | No | Yes (6 ± 1 fold) |

In a second experiment, two animals each were given cells which had been treated with 0.2% serum and 3H (no insulin, hydrocortisone, TSH) for 6 days plus or minus MMI for 72 hours. As evaluated by microscopy no animal had thyroid cells after 60 days and none had a TSH response in either assay. This would be expected since MMI action appears to require serum and since class I is maximally expressed under these conditions, in vitro, in the absence of serum, insulin, hydrocortisone and TSH (Saji et al. (1992 (b)).

In a third experiment, FRT rat thyroid cells, a line of cells with no TSH receptor mRNA and no thyroid function (Ambesi-Impiombato F. S., Coon H. G. (1979) *Int Rev Cytol Suppl.* 10:163–171; Akamizu T, et al., (1990) *Proc. Natl. Acad. Sci. USA*, 87:5677–5681), were permanently transfected with human TSHR cDNA using a neomycin selection procedure (Van Sande J. et al., (1990) *Mol. Cell. Endocrinol*, 74:R1–R6). The transfected FRT thyroid cells were treated with, as were the FRTL-5 cells, 5 mM MMI for 72 hours and transplanted into the backs of Balb/c mice as described above. Sixty days later cells were isolated and shown to have a TSR-increased cAMP response as described above. Control cells with transfected TSHR cDNA which were not treated with MMI or control FRT cells with no TSHR cDNA, when similarly implanted and evaluated, did not exhibit a TSR-increased cAMP level. This indicates that a transfected gene can survive the MMI procedure to transplant cells.

EXAMPLE 6

Assessment of the Effect of MMI on MHC-Class I Expression by Gel Shift Assay

Materials

Purified bovine TSH was from the NIH program (NIDDK-bTSH-I-1, 30U/mg) or was prepared as described previously (Kohn, L. D. and Winand, R. J. (1975) *J. Biol. Chem.*, 250:6503–6508). Insulin, hydrocortisone, human transferrin, somatostatin, glycyl-L-histodyl-L-lysine acetate were from (Sigma Chemical Co. St. Louis, Mo. ). [$^{125}$I] cAMP radioimmunoassay kits, [$\alpha$-$^{32}$P]dCTP (3000 Ci/mmol) and [$^{32}$P]UTP (3000 Ci/mmol) were from Du Pont/New England Nuclear (Boston, Mass.).

Cell Culture

FRTL-5 rat thyroid cells (Kohn LD. et al., U.S. Pat. No. 4,609,622; Ambesi-Impiombato ES., U.S. Pat. No. 4,608, 341) are grown as described. These cells do not proliferate in the absence of TSH, yet remain viable for prolonged periods in its absence. Their doubling time was approximately 36±6 hours; and, after 6 days in medium with no TSH (5H) and 5.0% serum, $1 \times 10^{-10}$ mol/L TSH elevated iodide uptake 8–10 fold and thymidine incorporation>10 fold. Cells were diploid, between their 5th and 25th passage in most experiments, and were routinely grown in Coon's modified F12 medium supplemented with 5% calf serum, 1 mmol/L nonessential amino acids (GIBCO) and a mixture of 6 hormones (6H medium): TSH ($1 \times 10^{-10}$ mol/L), insulin (10 mg/L), hydrocortisone 1(nmol/L), human transferrin (5 mg/L), somatostatin (10 µg/L) and glycyl-L-histidyl-L-lysine acetate (10 µg/L) (Kohn, L. D. et al. U.S. Pat. No. 4,609,622; Ambesi-Impiombato, E. S. U.S. Pat. No. 4,608, 341). They were passaged every 7–10 days and provided fresh media every 2 or 3 days. In individual experiments, cells were shifted to medium with no TSH (5H), to medium with neither TSH and or insulin (4H), or to medium with no TSH, no insulin, and no hydrocortisone (3H) plus either 5% or 0.2% serum for 4–6 days before use.

Cell extracts

Cells were grown in 6H medium with 5% calf serum medium for 6–7 days to 70–80% confluence, then shifted to 5H medium with 5% calf serum for 5 days. TSH ($1 \times 10^{-10}$M) and/or MMI (5 mM) were added as appropriate for 40–44 hours. Cells were then harvested and extracts were made by a modification of a method of Dignam, J. et al. (1983) *Methods in Enzymology*, 101:582–598. In brief, cells were harvested by scraping after being washed twice with cold phosphate-buffer saline (PBS). Subsequently they were pelleted, washed in cold PBS and then pelleted again. The pellet was resuspended in Dignam buffer C (20 mM Hepes buffer at pH 7.9, 1.5 mM $MgCl_2$, 0.42M NaCl, 25% glycerol, 0.5mM dithiotreitol, 0.5 mM phenylmethylsulfonylfluoride, 1 µg/ml leupeptin, 1 µg/ml pepstatin). The final NaCl concentration was adjusted on the basis of cell pellet volume to 0.42M and cells were lysed by repeated cycles of freezing and thawing. Extracts were then centrifuged at 10,000×g at 4° C. for 20 min. The supernatant was recovered, aliquoted and stored at −70° C.

Gel Mobility Shift Assay

Binding reactions were performed in a volume of 20 µl for 30 min at room temperature. The typical reaction mixture contains 1.5 fmol of $^{32}$P DNA, 3 µg of cell extracts, 3 µg of poly (dI-dC) in 10 mM Tris-Cl (pH 7.9), 1 MM $MgCl_2$, 1 mM dithiothreitol, 1 mM EDTA, and 5% glycerol. Unlabeled competitor (a 100- to 1000-fold excess of double-stranded oligonucleotides or 200-fold excess of PD1 promoter fragments) was added to the appropriate control binding reactions 20 min before the $^{32}$P to insure specificity. After incubation, reaction mixtures were subjected to electrophoresis in 4% polyacrylamide gels for 90–120 min at 160V in 0.5×TBE (Sambrook, J., et al., (1989) then dried and autoradiographed. Probes were labeled by Klenow enzyme (In Vitro labeling kit, Amersham), following manufacturer instructions, and then purified through G-50 columns (5 primed→3 Prime).

Positive and negative regulatory elements have been identified in the promoter of the swine MHC class I gene, PD1 (Singer and Maguire (1990)). The activity of these enhancers and silencer regions is mediated by transacting factors (Singer and Maguire (1990)). Two regulatory domains have been identified in the 5' flanking region of the PD1 gene. One regulatory domain is between approximately −1 and −300 bp from the transcriptional start site. This region contains an interferon response element and a major enhancer, as well a site homologous to a cyclic AMP response element (CRE) element. Studies using gel mobility shift assays have demonstrated that TSH/CAMP-induced or modified proteins interact with this region and can regulate transcription initiation (Saji et al. (1992a)). Another complex regulatory region, showing overlapping silencer and enhancer activity, has been mapped between −690 and −769 base pairs upstream of the promoter (Weissman, J. D. and Singer, D. S. (1991) *Mol. Cell. Biol.* 11:4217–4227). The enhancer and silencer elements are linked to tissue specific expression and tissue specific levels of the Class I gene (Weissman, J. D. and Singer, D. S. (1991)).

The Saji et al (1992b) study showed reduced expression of MHC Class I gene in rat FRTL-5 cells treated with MMI. This study also showed that the effect of MMI in MHC Class I expression was at the level of transcription. The FRTL-5 thyroid cell system is therefore a good system to identify the regulatory DNA sequence elements and trans-acting factors involved in the MMI effect. PD1 Gel shift mobility assays were performed using the 5' flanking region of the PD1 gene and cell extracts from FRTL-5 cells treated with MMI, TSH and MMI plus TSH.

FIG. 9 shows the sequence of the PD1 promoter with the 151, 114, 140 and 238 regions of the 5' portion of the PD1 promoter designated as indicated (Weismann, J. D. and Singer, D. S. (1991)). FIG. 10 shows the silencer and enhancer regions of the 140 region with oligonucleotides used to map the region for the activity of the gel shifts. The silencer region of relevance is noted by the opposite arrows separated by a TTF-2 like, insulin-sensitive element. FIG. 10 shows the alignment of the 114, 140, and the 105 region of the 238 region of the PD1 promoter to show sequence homology. The silencer region is indicated by arrows separated by TTF-2 like region. These fragments were derived from the PD1 promoter of the PDI Class I MHC gene (Singer D. S. et al. (1982) *Proc. Natl. Acad. Sci. USA*, 79:1403–1407).

FIG. 12 shows gel shifts using the radiolabelled 140 (FIGS. 12A and 12D), 114(FIG. 12B) and 151(FIG. 12C) fragments noted in FIG. 9. The complex affected by MMI is denoted A. In FIG. 12A, 12B and 12C, lane 4 shows the complex formed between the silencer region (see FIG. 10 and below) and cell extracts from FRTL-5 rat thyroid cells maintained in the presence of 5H medium (no TSH) plus 5% serum. The effect of the addition of 5 mM MMI for 24 hours prior to extract preparation from cells maintained in 5H medium is shown in lane 5 of FIGS. 12 A–D. The effect of the addition of $1 \times 10^{-10}$M TSH for 24 hours prior to extract preparation from cells maintained in 5H medium is shown in lane 6 in FIGS. 12 A–C. The effect of the addition of 5 mM MMI plus $1 \times 10^{-10}$M TSH for 24 hours prior to extract preparation from cells maintained in 5H medium is noted in lane 7 in FIG. 12A and 12B. The effect of the addition of $1 \times 10^{-10M}$ TSH for 7 days before extracts were prepared (6H, MMI-) is noted in lane 3 in FIG. 12A–C. The effect of the addition of $1 \times 10^{-10}$M TSH plus 5mM MMI for 24 hours before extracts were prepared (6H, MM1+) is noted in lane 2 in each case. Lane 1 in FIGS. 12 A–C contains the radiolabelled probe alone. The ability of 200-fold excess concentration of unlabeled 151 fragment to compete A complex formation with the 151 radiolabelled fragment is shown in lane c, FIG. 12C. Competition to inhibit MMI-sensitive A complex formation by 200-fold higher concentrations of unlabeled 105 (lane a, FIG. 12C), 140 (lane b, FIG. 12C) and 114 (lane d, FIG. 12D) are noted showing that the A complex formed with each complex is the same. In panel D, lane e shows the basal A complex formed between the silencer region (see FIG. 10 and below) and cell extracts from FRTL-5 rat thyroid cells maintained in the presence of a 3H medium plus 0.2% calf serum. In contrast to cells maintained in the 5H plus 5% serum case (FIG. 12(A)), MMI (lane f), TSH (lane g) or both together (lane h) added to cells for 24 hours does not significantly affect A complex formation in 3H medium (FIG. 12D). 3H medium has no insulin as well as no TSH. The ability of 200-fold excess concentration of unlabeled 105 (lane i) to inhibit formation of the MMI-insensitive A complex in 3H medium shows that same complex appears to be involved, but the absence of insulin and/or serum in 3H medium prevents the TSH and MMI inhibitory effect. The lack of A complex formation in the absence of the 3H cell extracts is noted in lane j.

FIG. 14(A) shows gel shifts using the radiolabelled 238 fragment noted in FIG. 9 and cell extracts from FRTL-5 rat thyroid cells maintained in the presence of a 5H hormone mixture (no TSH) plus 5% serum (5H Basal) Lane 2). The complex affected by MMI is denoted A; inhibition of the formation of this complex by cellular extracts from FRTL-5 cells treated for 24 hours with 5 mM MMI plus $1 \times 10^{-10}$M TSH is noted in lane 14. The 238 construct encompasses the 105 construct (see FIG. 9); complex A forms with the 105 portion of the 238 construct as evidenced by the ability of a 200-fold excess concentration of unlabeled 105 over radiolabelled 238 to inhibit complex A formation (lane 3). The A complex in lane 2 is formed between the silencer region (see FIG. 10 and above) and is the same as that formed with the 114, 140, and 151 constructs (FIG. 12) as evidenced by the following. First, a 200-fold higher concentration of unlabeled 114 (lane 4) and 140 (lane 5), compared to radiolabelled 238, inhibited A complex formation; a 200-fold higher concentration of 151 was a partial inhibitor (lane 6). Second, a 1000-fold concentration of double stranded oligonucleotide with the sequence of the silencer region (S2 in FIG. 10), relative to radiolabelled 238, inhibited A complex formation; the same concentration of double-stranded oligonucleotide mimicking the sequence of the enhancer element (E1 in FIG. 10) had no effect on A complex formation. Oligonucleotides with modifications of the silencer sequence (S1, S3, S6, S7, and S8 in FIG. 10) were partial inhibitors at the 1000-fold concentration (lanes 9–13). The inhibition by S1 (lane 12) suggested that mutation of only one of the end repeats denoted by the arrows in FIG. 10 is enough to decrease inhibition; the partial inhibition by S8 (lane 10) suggested that the element which resembles the sequence reactive with TTF-2 in the thyroglobulin promoter (Santisteban, P., et al., and *Mol. Endocrinol.* 6:1310–1317, 1992) and that is between the inverted repeats (FIG. 10) is also important in formation of the A complex. This conclusion is supported by the result in lane 7. The presence of a 1000-fold concentration of the K oligonucleotide which mimics the sequence of the thyroid transcription factor-2 (TTF-2)-reactive element in the thyroglobulin promoter (Santisteban, P. et al., *Mol. Endocrinol.* 6:1310–1317, 1992) enhanced A complex formation and by the result in lane 15 which showed that a 1000-fold higher concentration of unlabeled oligonucleotide K was able to reverse the MMI/TSH action. Thus, decreased formation of the MMI-sensitive A complex requires TTF-2 and insulin, consistent with the data in FIG. 12D. The K oligonucleotide "sties up" insulin-induced TTF-2 which results in increased complex formation and loss of the MMI effect, i.e. there is a requirement for insulin.

FIG. 14(B) further demonstrates the importance of TTF-2 to the MMI action and provides an additional means to assay the MMI effect. FIG. 14(B) shows gel shifts using the radiolabelled K oligonucleotide (TGACTAGCAGAGAAAACAAAGTGA) and cell extracts from FRTL-5 rat thyroid cells maintained in the presence of a 5H hormone mixture (no TSH) plus 5% serum (5H Basal) (Lane 16). The upper FRTL-5 cell protein/DNA complex formed is inhibited by treating cells for 24 hours with 5 mM MMI (lane 17), with $1 \times 10^{-10}$ TSH (lane 18) and with 5 mM MMI plus $1 \times 10^{-10}$M TSH (lane 19). The TTF-2 upper protein/DNA complex is therefore necessary for MMI action and important in A complex formation noted in FIG. 14A. Inhibition of its formation is a means to assay the MMI effect and supports the insulin-dependency of MMI action.

The complexes detected below the A complex in FIGS. 12 A–D and FIG. 14 A–B are believed to be enhancer complexes (uppermost bands below the A complex) or nonspecific complex. The intense signal at the bottom of the autoradiographs in FIGS. 12 A–D and FIG. 14 A–B was unbound probe.

Taken together these results suggest that inhibition of complex formation can be used as an indicator of MMI or other drugs to down regulate MHC Class I transcription.

The A complex is believed to be composed of different proteins. The different proteins are important in determining the level of tissue specific complexes between tissues. TSH induced the formation of a new thyroid specific complex in the −200 to −1 region of the PD1 promoter. This complex was also increased by 5 mm MMI and involved a TTF-2-like transcription factor. This complex was increased as the A complex decreases. Its formation was associated with TATAA box activity. We propose this thyroid specific protein/DNA complex dominates the tissue-specific silencer/enhancer complex (FIG. 10) and decreases gene expression by decreasing the initiation of transcription of the Class I gene.

EXAMPLE 7

Assessment of the Effect of MMI on MHC Class I Expression by CAT Assay

Plasmid construction, DNA probes and oligonucleotides

The full length PD1 promoter, PD1 CAT construct pH(−38), inserted into the multicloning site of pSV3CAT, has been previously described (Erhlich, R. et al. (1989) *Immunogenetics* 30:18–26). Sequential deletion mutants of the full length PD1 promoter, inserted into the multicloning site of pSV3CAT, have been previously described (Singer and Weismann (1991); Saji et al (1992a); Saji et al. (1992b)). Briefly, a nested series of 5' deletions of the upstream regulator region of the PD1 gene were generated by Bal31 digestion; the series 5' termini ranged from −1012 base pairs to −68 base pairs; all had a common 3' boundary at +15 base pairs. The deletion series was also cloned into the pSV3CAT reporter construct to assess promoter activities (Singer and Weisman (1991); Maguire, J. et al. (1992) *Mol. Cell. Biol* 12:3078–3086).

FIG. 13 shows transfection data with chloramphenicol acetyltransferase (CAT) chimeras showing that MMI inhibits full length PD1 promoter activity.

Rat FRTL-5 thyroid cells were put in fresh 6H medium containing 5% calf serum 12 hours before transfection by the electroporation method described previously (Saji et al 1992 b). In brief, FRTL-5 cells were grown to 80% confluence, harvested, washed, and suspended at $1.5 \times 10^7$ cells/ml in 0.8 ml electroporation buffer (272 mM sucrose, 7 mM sodium phosphate at pH 7.4, and 1 mM $MgCl_2$). Twenty Mg of the full length CAT construct were added with 5 μg PSVGH. Cells were then pulsed (330 volts, capacitance 25 μFD), plated (approximately $6 \times 10^6$ cell/dish), and cultured for 12 hours in 6H medium containing 5% calf serum medium. At that time, cells were placed in 5H medium plus 5% calf serum (control), 5H medium plus 5% calf serum plus 5 mM MMI (MMI+), 6H medium plus 5% calf serum (TSH+), or 6H medium plus 5% calf serum plus 5 mM MMI (MMI/TSH). After 40 hours they are harvested. Cell viability was approximately 80%. Medium was taken for hGH radioimmunoassay to monitor transfection efficiency. (Nichols Institute, San Juan Capistrano, Calif.) and cells were harvested for CAT assays which used 20–50 μg cell lysate in a final volume of 130 μl. Incubation was at 37° C. for 2 or 4 hours; acetylated chloramphenicol was separated by thin layer chromatography (TLC) and positive spots on TLC plates were cut out and quantitated in a scintillation spectrometer. Data are expressed as the ratio of CAT activity to GH activity. The full length PD1 promoter includes the 151, 114, 140, and 238 regions (FIG. 9). As shown in FIG. 13 treatment with MMI (▨) TSH and MMI (▧) and TSH (▩) decrease CAT activity relative to the control (■) CAT activity of the chimeric CAT constructs of the sequential deletion mutants can also be used on CAT assays to assay the effect of MMI on Class I promoter activity. CAT activity is, therefore, another way to assay the effect of MMI on class-I promoter activity and can be used for evaluating other agents able to mimic MMI in therapeutic actions related to treatment of autoimmune disease or transplantation therapy.

Although the present invention has been described in some detail by way of illustration and example for purposes of clarity of understanding, it will be obvious that certain changes and modifications may be practiced within the scope of the appended claims.

We claim:

1. A method for assessing the therapeutic potential of a candidate drug for suppressing MHC Class I molecules and preventing or treating transplantation rejection in a transplant recipient comprising the steps of:
   (a) treating a population of mammalian cells with said candidate drug capable of suppressing MHC Class I molecules;
   (b) transplanting said cells into a mammal;
   (c) excising said cells from said mammal; and
   (d) evaluating said transplanted cells for viability, wherein the viability of said cells indicates said candidate's drug potential in preventing or treating transplantation rejection.

2. The method of claim 1, wherein said mammalian cells are selected from the group consisting of mammalian cell thyrocytes, hepatocytes, neural tissue, muscle, fibroblasts, adipocytes, and HELA cells.

3. The method of claim 1, wherein said mammal is a rodent.

4. The method of claim 1, wherein said mammalian cells are FRTL-5 rat thyroid cells.

5. The method of claim 1, wherein said drug is selected from the group consisting of methimazole, methimazole derivatives, carbimazole, propylthiouracil, thionamides, thiourelylenes, thioureas and thioruea derivatives.

* * * * *